(12) United States Patent
Diamond et al.

(10) Patent No.: US 7,297,501 B2
(45) Date of Patent: Nov. 20, 2007

(54) METHOD AND DEVICES FOR RUNNING REACTIONS ON A TARGET PLATE FOR MALDI MASS SPECTROMETRY

(75) Inventors: Scott L. Diamond, Bala Cynwyd, PA (US); Dhaval Gosalia, Philadelphia, PA (US)

(73) Assignee: University of Pennsylvania, Philadelphia, PA (US)

( * ) Notice: Subject to any disclaimer, the term of this patent is extended or adjusted under 35 U.S.C. 154(b) by 147 days.

(21) Appl. No.: 11/013,302

(22) Filed: Dec. 15, 2004

(65) Prior Publication Data

US 2005/0153344 A1    Jul. 14, 2005

Related U.S. Application Data

(63) Continuation-in-part of application No. 10/036,066, filed on Nov. 7, 2001.

(60) Provisional application No. 60/614,145, filed on Sep. 29, 2004, provisional application No. 60/529,643, filed on Dec. 15, 2003, provisional application No. 60/266,042, filed on Feb. 2, 2001, provisional application No. 60/309,999, filed on Aug. 3, 2001, provisional application No. 60/313,380, filed on Aug. 17, 2001, provisional application No. 60/313,368, filed on Aug. 17, 2001, provisional application No. 60/313,377, filed on Aug. 17, 2001, provisional application No. 60/322,619, filed on Sep. 17, 2001.

(51) Int. Cl.
*G01N 33/53* (2006.01)

(52) U.S. Cl. .................................................. 435/7.1

(58) Field of Classification Search ................ 435/7.1, 435/4, 7.42, 283.1, 287.3; 436/514, 515, 436/518; 356/244, 246; 422/50, 58, 63, 422/56
See application file for complete search history.

(56) References Cited

U.S. PATENT DOCUMENTS

| 5,345,079 A | 9/1994 | French et al. |
| 5,808,300 A | 9/1998 | Caprioli |
| 6,027,890 A | 2/2000 | Ness et al. |
| 6,228,390 B1 | 9/2001 | Siuzdak et al. |
| 6,316,266 B1 | 11/2001 | Nelson et al. |
| 6,358,692 B1 | 3/2002 | Jindal et al. |
| 6,569,383 B1 | 5/2003 | Nelson et al. |
| 6,710,335 B2 | 3/2004 | Ellson et al. |
| 6,737,024 B1 | 5/2004 | Eipel et al. |
| 2002/0142351 A1 | 10/2002 | Diamond |
| 2002/0195558 A1 | 12/2002 | Elison et al. |
| 2003/0054564 A1 | 3/2003 | Diamond |

OTHER PUBLICATIONS

Caprioli, R.M., J. Mass Spectrometry 38:1081-1092 (2002).
Caprioli, R.M., Electrophoresis 23, 3125-3135 (2002).

*Primary Examiner*—Ann Y. Lam
(74) *Attorney, Agent, or Firm*—Pepper Hamilton LLP

(57) ABSTRACT

A peptide or protein microassay method and apparatus in which a wide variety of chromogenic or fluorogenic peptide or protein substrates of interest are individually suspended or dissolved in a hydrophilic carrier, with aliquots of each substrate being deposited in an array or microarray of reaction loci, or "dots." Each dot, therefore, provides an individual reaction vessel containing the peptide or protein of interest, to which a biological sample may be applied for assay purposes. The sample is applied to the array or microarray of dots by one of a variety of focused sample application techniques, including aerosolizing or misting of the sample, or target application of the sample, onto each dot without creating fluid channels between the dots which would cause cross-contamination. In additional aspects, the present invention provides methods of transferring samples from an electrophoretic gel to a target plate for subsequent MALDI MS analysis. Chemical reactions of interest can be run directly on the target plate, and the reaction products on the target are then prepared for MALDI MS analysis by drying and aerosol deposition of matrix material, without the need for salt removal and additional processing steps.

22 Claims, 32 Drawing Sheets

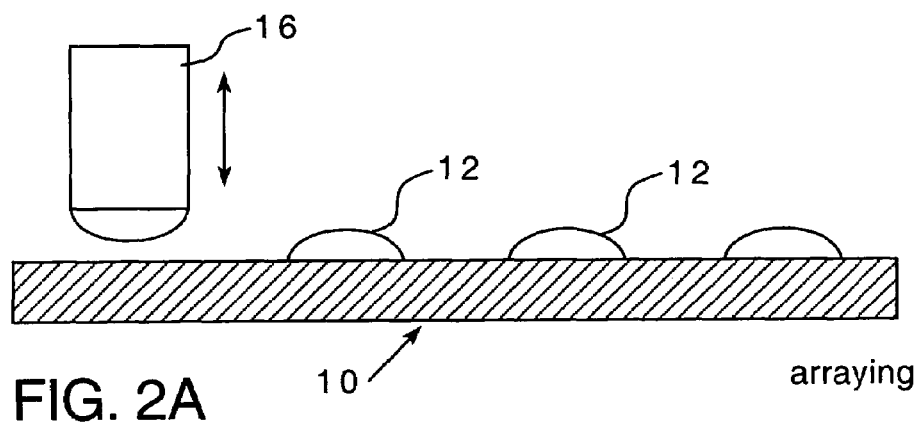
FIG. 2A  arraying
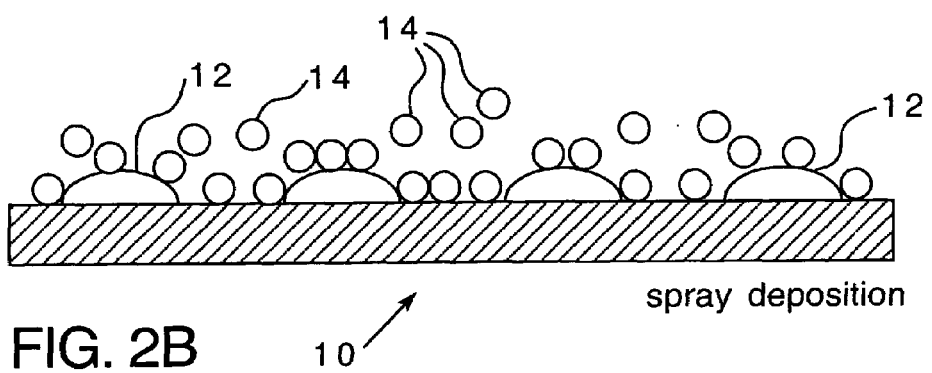
FIG. 2B  spray deposition
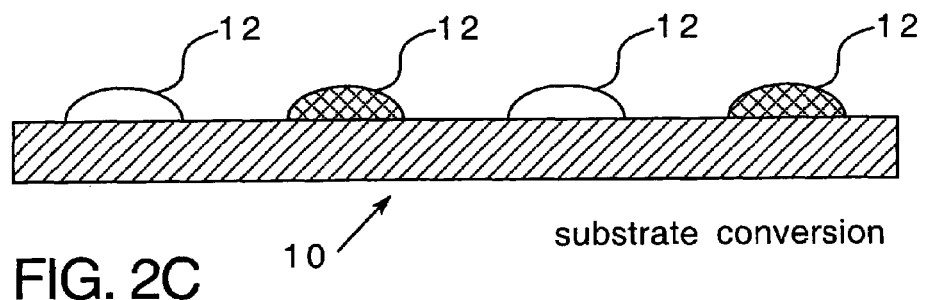
FIG. 2C  substrate conversion

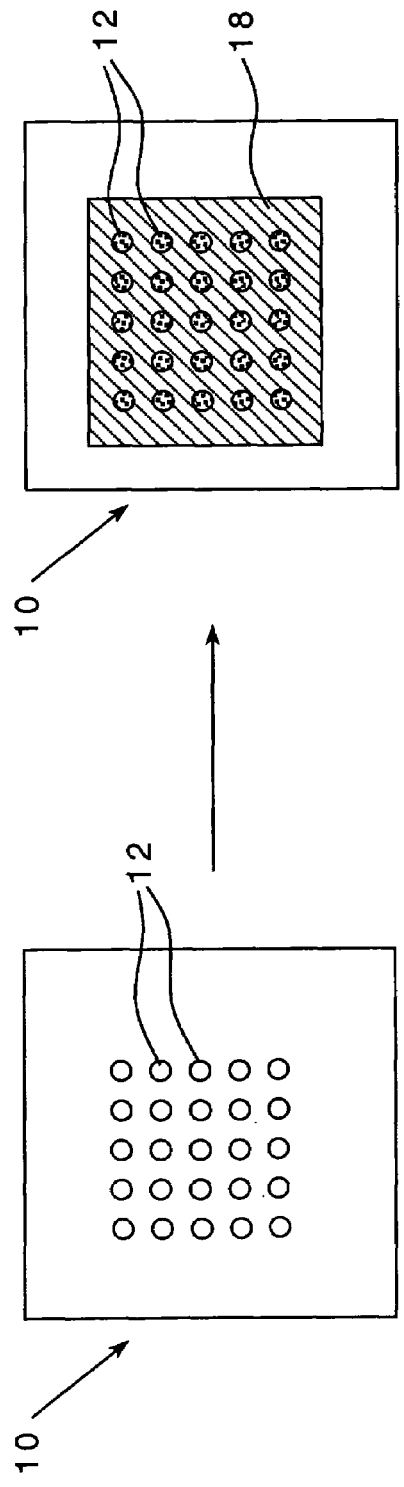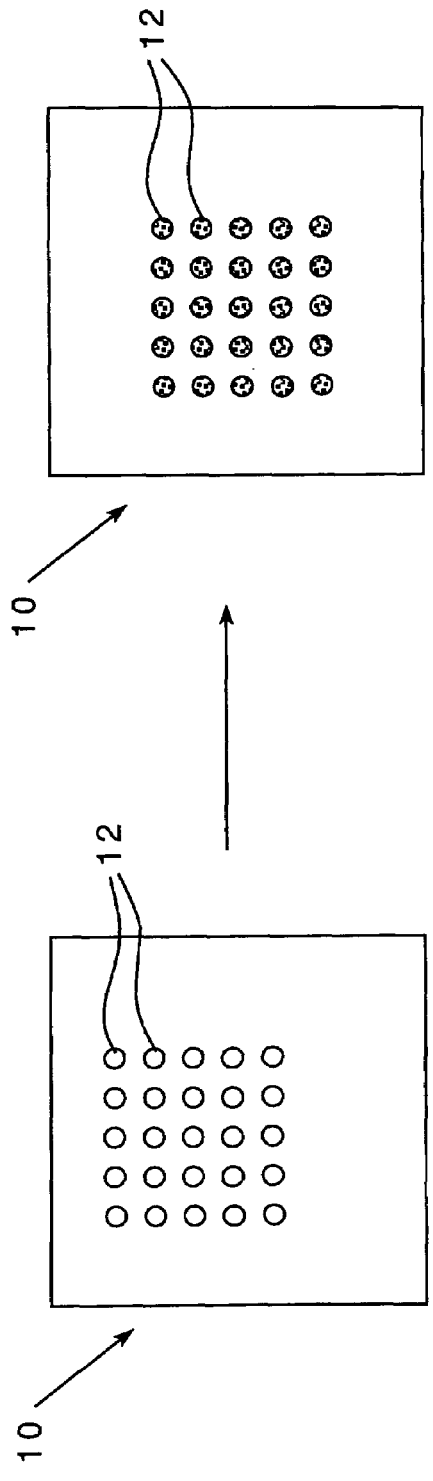
FIG. 3A
FIG. 3B

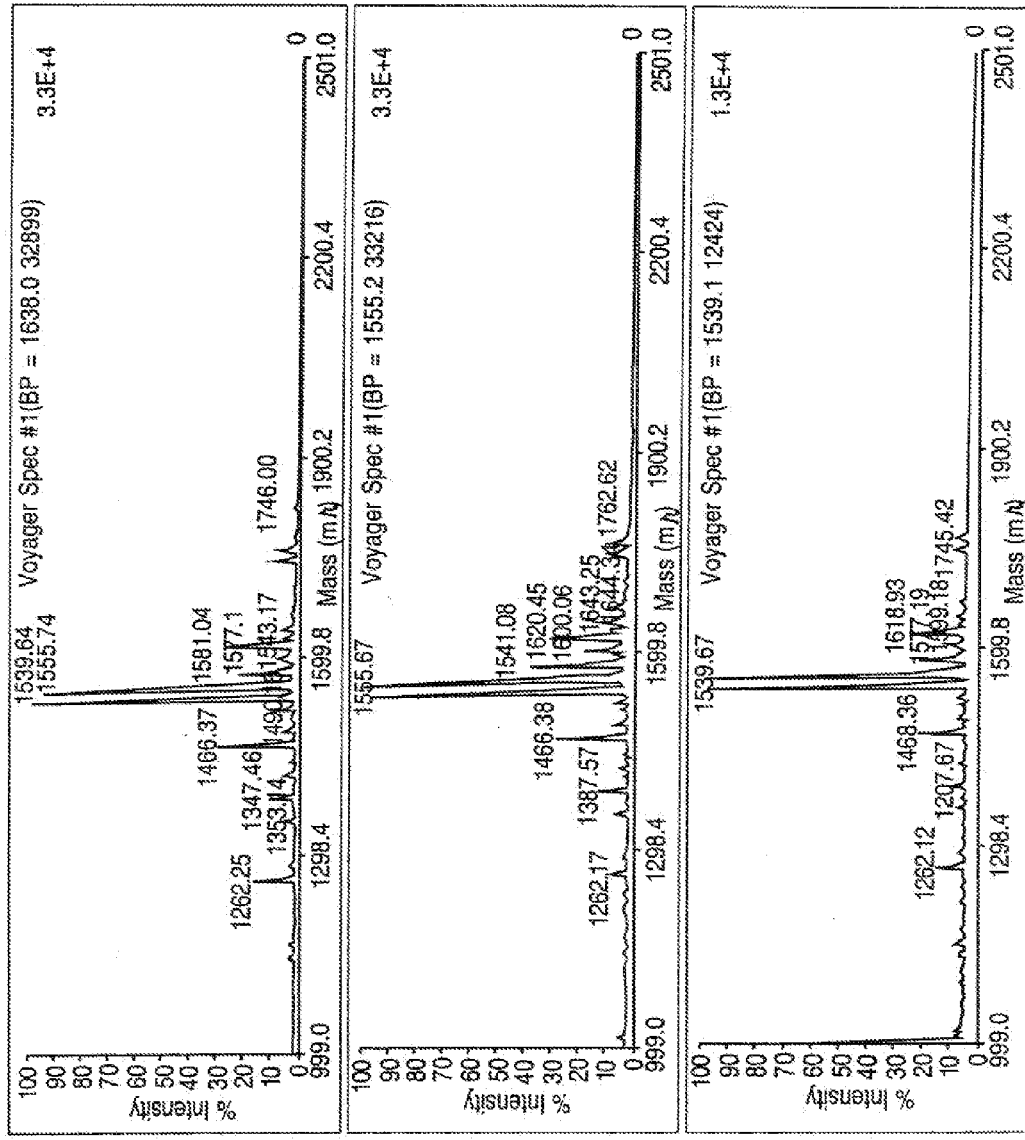

Figure 27F:
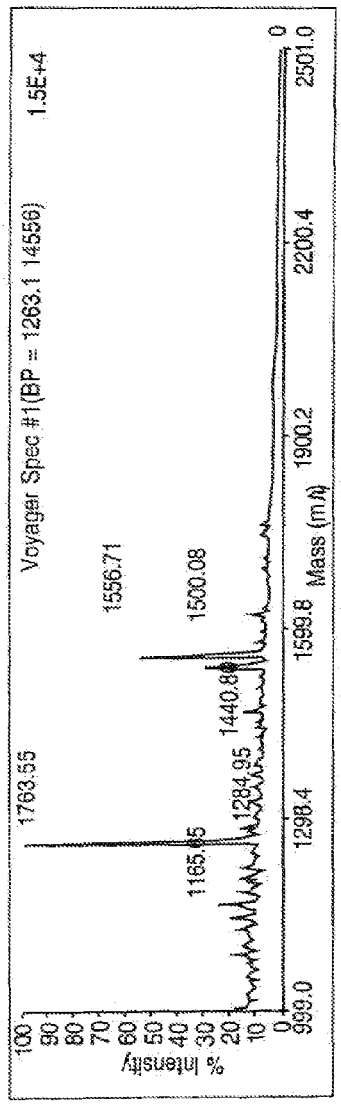
Figure 27G:
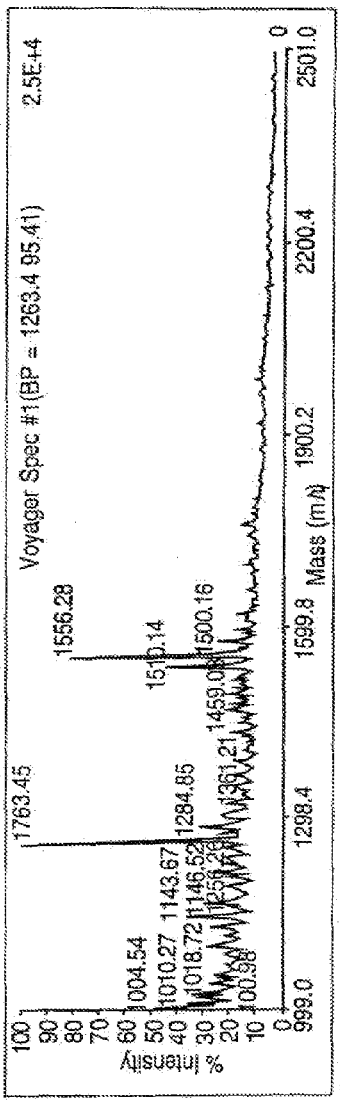
Figure 27H:
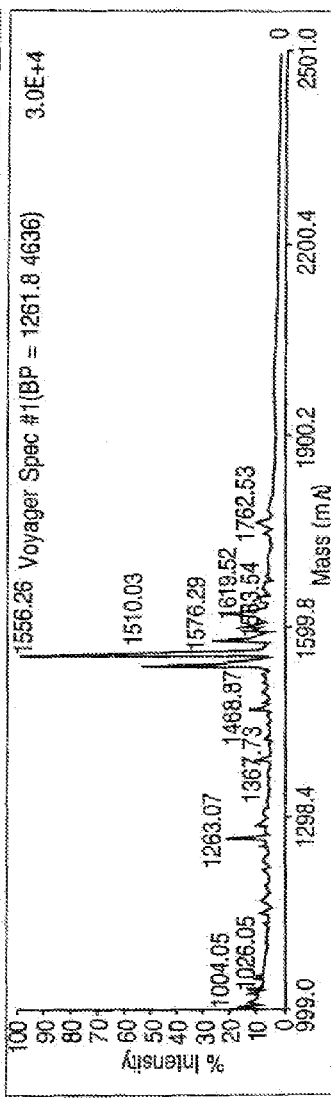
Figure 27I:
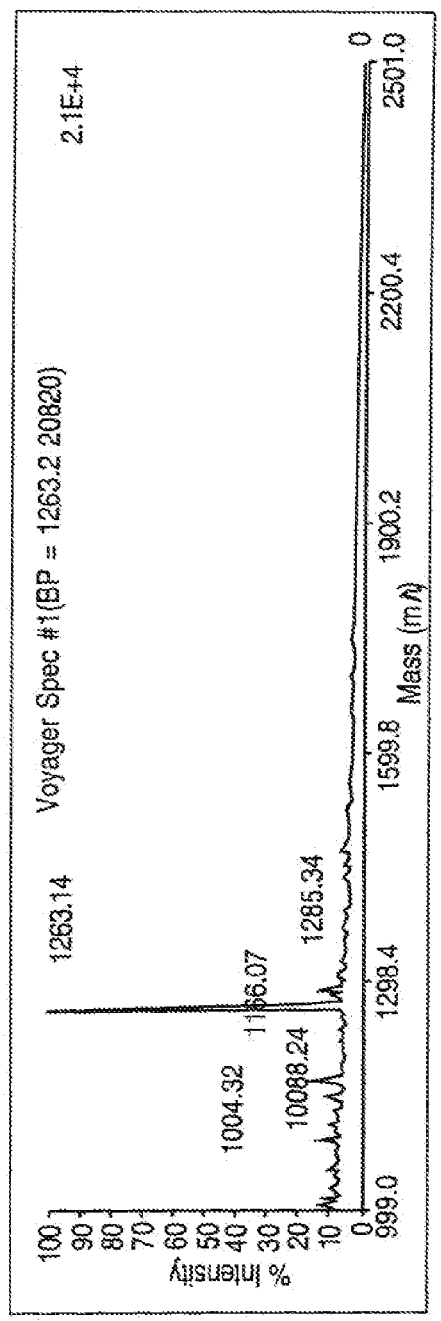
Figure 27J:
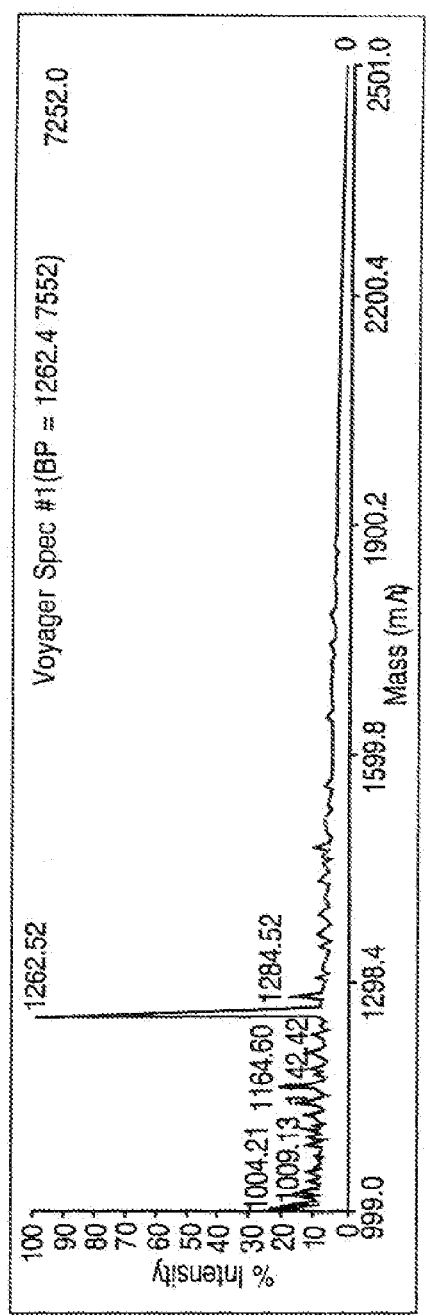
Figure 27K:
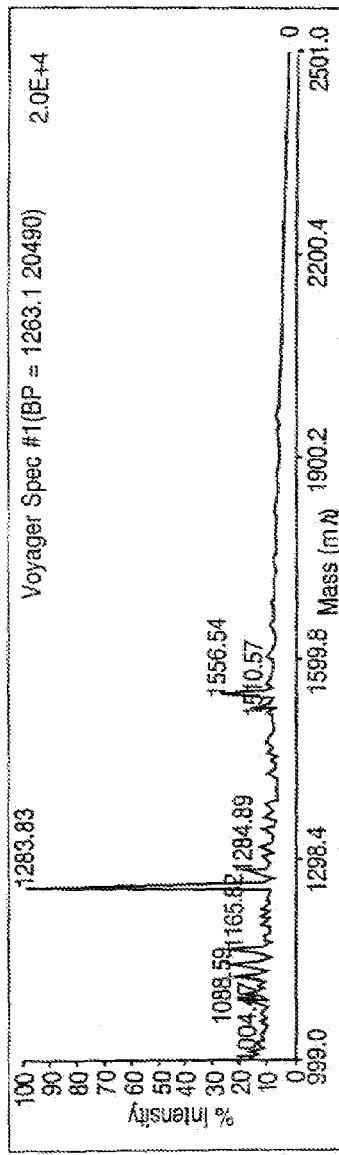
Figure 27L:
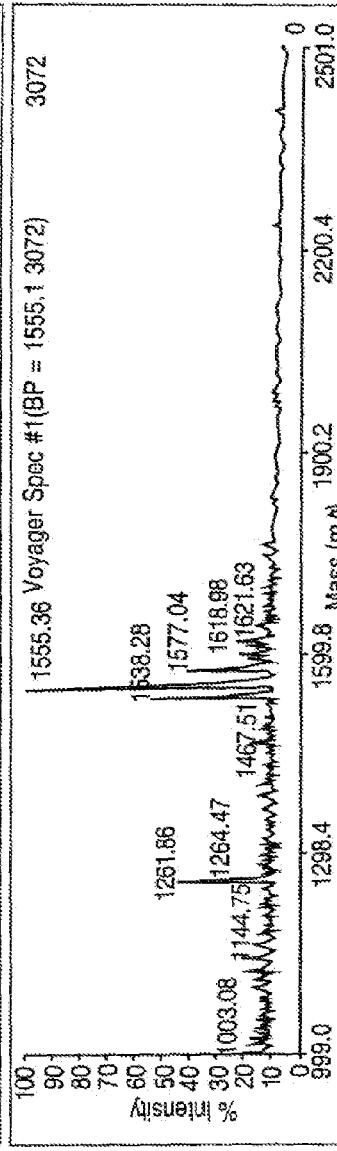
Figure 27M:
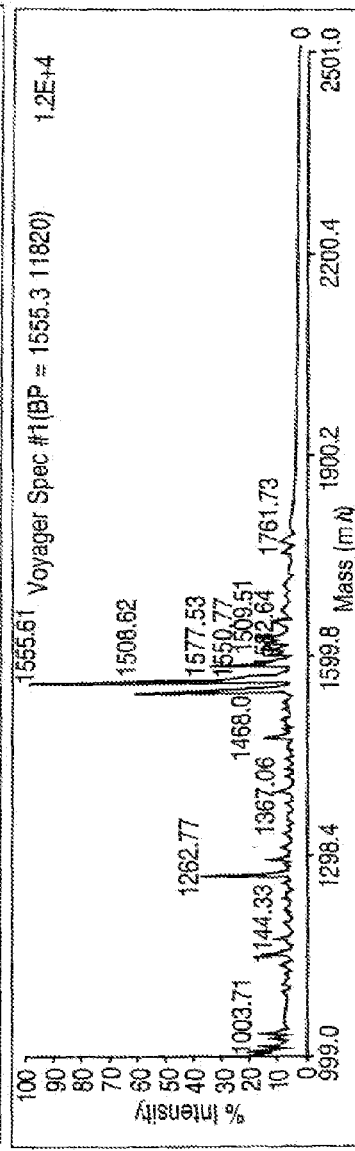
Figure 27N:
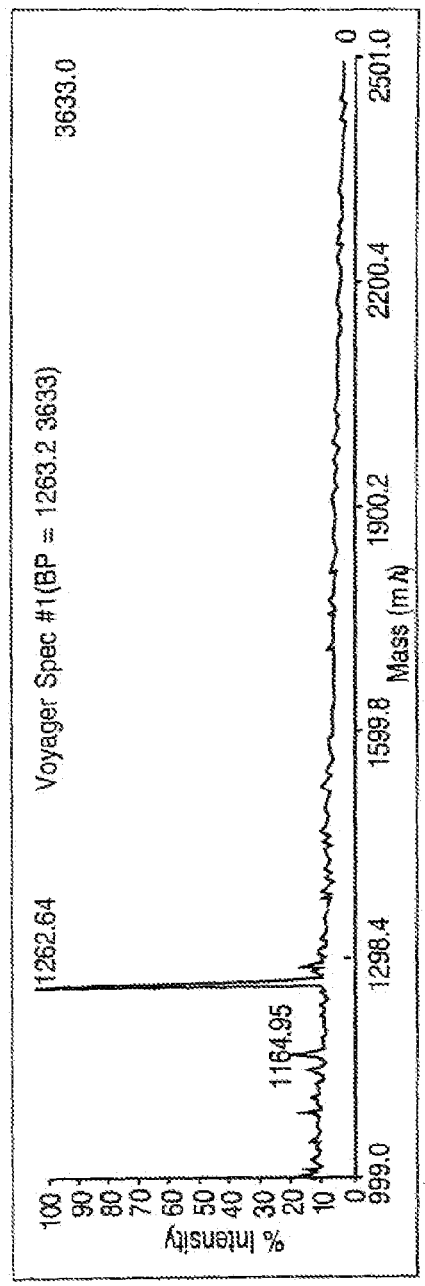

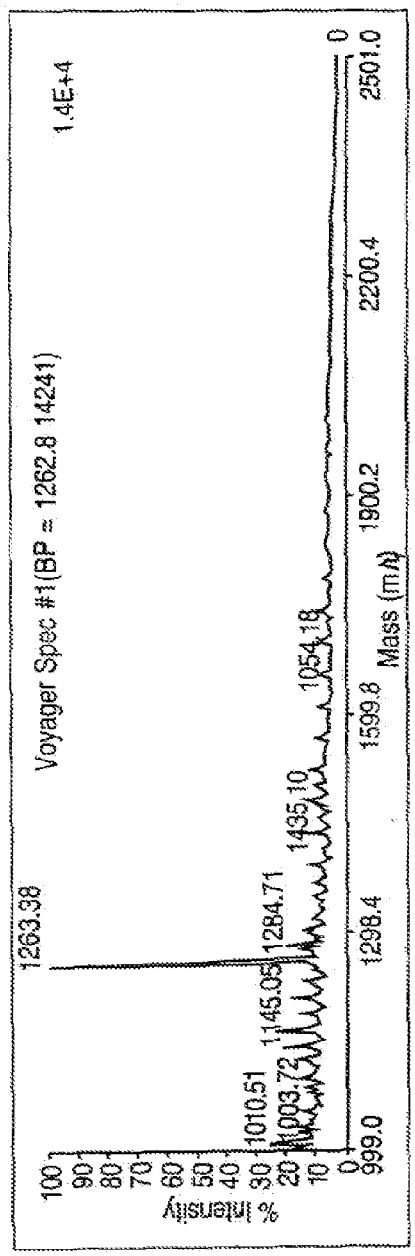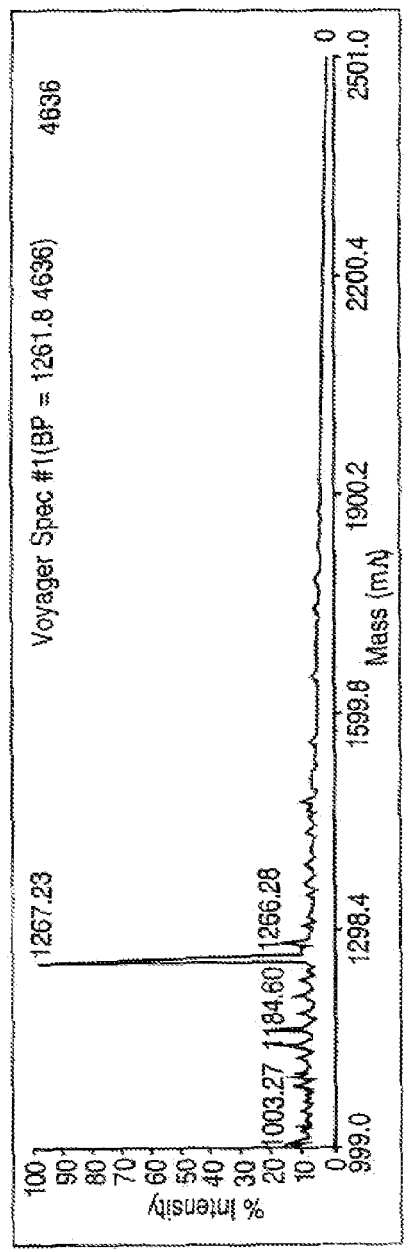
FIG. 27D  Fibrinogen 18mg/ml Control
FIG. 27E

Fibrinogen 3 mg/ml

Fibrinogen 3mg/ml
Control

Fibrinogen 0.75 mg/ml

Fibirinogen 0.75mg/ml
Control

METHOD AND DEVICES FOR RUNNING REACTIONS ON A TARGET PLATE FOR MALDI MASS SPECTROMETRY

CROSS REFERENCE TO RELATED APPLICATIONS

This application claims priority to U.S. Provisional Patent Application Ser. No. 60/529,643 filed Dec. 15, 2003, and to U.S. Provisional Patent Application Ser. No. 60/614,145 filed Sep. 29, 2004, and is also a Continuation-In-Part of U.S. patent application Ser. No. 10/036,066 filed Nov. 7, 2001, which claims priority to each of the following United States (U.S.) Provisional Patent applications: U.S. Provisional Patent Application Ser. No. 60/266,042 filed Feb. 2, 2001; U.S. Provisional Patent Application Ser. No. 60/309,999 filed Aug. 3, 2001; U.S. Provisional Patent Application Ser. No. 60/313,380 filed Aug. 17, 2001; U.S. Provisional Patent Application Ser. No. 60/313,368 filed Aug. 17, 2001; U.S. Provisional Patent Application Ser. No. 60/313,377 filed Aug. 17, 2001; and U.S. Provisional Patent Application Ser. No. 60/322,619 filed Sep. 17, 2001, each of which is incorporated herein by reference.

BACKGROUND OF THE INVENTION

1. Field of the Invention

The invention relates to a microassay chip and method for analysis by means of peptides or proteins for use in biological research and biomedical diagnosis. In an additional aspect, the invention relates to methods of transferring molecules of interest from an electrophoretic gel directly to a target plate for MALDI mass spectrometry analysis. In a further aspect, methods for running chemical reactions on a target plate, methods of preparing samples for MALDI mass spectrometry analysis, and methods of depositing MALDI matrix on a target plate are also included.

2. Description of Related Art

In biological research, biomedicine and industrial applications, large scale genomic evaluation for the detection of specific genes or DNA sequences within a genome, specific gene mutation such as single nucleotide polymorphisms (SNP), and MRNA species are well-established methodologies. These methodologies utilize DNA chips and microarrays on which specific nucleic acid sequences are either synthesized or deposited at individual highly localized positions on an array. These arrays containing the nucleic acid sequences find support on solids such as silicon or glass, or materials such as nylon membranes. The sequences can exist in the array on the order of $10^3$ or $10^4$ individual microsamples because individual "dots" or "pixels" have submillimeter characteristic lengths. While these chips have many applications for detecting the presence of and identifying genes in a genome (genotyping) or evaluating patterns of gene regulation (MRNA profiling) in cellular and tissue systems, these nucleic acid-based systems provide no information about the activity or regulation of the gene product, i.e., the synthesized protein.

Currently, DNA chips and microarrays allow genotyping and expression profiling, without rendering information about the activities of enzymes which can be regulated by phosphorylation or cleavage states. Protein chips to date have involved the capture of proteins to immobilized DNA sequences or libraries of immobilized peptides, antibodies or proteins. The three major formats for protein arrays employ plain glass slides, three-dimensional gel pad chips ("matrix" chips) or nanowell chips. None of these formats utilizes soluble substrates to identify numerous enzymes in a simple assay, however.

Proteomic methods typically utilize two-dimensional electrophoresis gels to separate proteins, followed by enzyme digest mapping and/or mass spectrometry to characterize relevant individual proteins in the gel. Neither DNA chips nor two-dimensional electrophoresis provide information about the activity of the protein or its reaction kinetics. For example, an enzyme may require phosphorylation or dephosphorylation in order to have full activity, and prior chip technologies do not provide this information.

Presently, enzyme activity can be measured by incubation of the enzyme with chromogenic substrates whose cleavage products become intensely colored and absorb light at a particular wavelength. Alternatively, the substrate may be a fluorogenic substrate whose cleavage results in leaving groups that are intensely fluorescent when excited at a particular wavelength (8-EX). Emission wavelengths of the leaving groups may span 10 to 20 nm above and below the maximum 8-EM. This prevents the use of more than two or three different fluorogenic substrates in a single sample to assay for three different enzymatic activities since the emission of each substrate may have significant overlap with the emission of the other substrates. Broad band emission results in color cross-talk and can render false signals. Thus, it is not possible to add 10 to 100 different fluorogenic substrates to a single fluid sample because the emissions would overlap severely. These reactions are typically monitored in cuvettes in a fluorimeter or plate-reader with working volumes of 0.2 to 3 ml. Thus, significant dilution of the sample occurs.

The evaluation of various proteins and/or enzymes within a small biological sample (1.0 to 100 nL) would be useful in analyzing the activity of those proteins and/or enzymes in a number of fields of study. In the field of cell biology and cancer, the timing of cell division is regulated by numerous cyclin-dependent kinases (cdk), cAMP-dependent kinases (PKA), cGMP-dependent kinases (PKG), and calcium-dependent protein kinases (PKC), tyrosine kinases, and tyrosine phosphatases. In the field of hematology, the function of blood is regulated by various coagulation factors, complement factors and fibrinolytic factors which are proteases and inhibitors necessary for thrombotic and thrombolytic mechanisms. During apoptosis (programmed cell death) various caspases are critical to the cascade of events. Similarly, neutrophil activation during sepsis, thrombosis or infection is coordinated with release of elastases, proteases or other enzymes. Tumor invasion and intimal hyperplasis can involve the activity of metal metalloproteases (MMPs) and tissue inhibitor of metalloproteases (TIMPs). Various viral activities (e.g., proteases) would be suitable for detection of drug screening of protease inhibitors.

Notwithstanding prior art developments in the areas of peptide and protein chips, therefore, the need for peptide or protein microarrays in diagnostic, prognostic and clinical medicine is large, and largely unmet. Prior art chips do not exist in which a great variety of suspended or soluble chromogenic or fluorogenic substrates may be simply deposited in an array on a support surface, with simple application of the sample fluid thereto for evaluation. At this writing, there are no known peptide or protein chips which can be directly fabricated using a standard contacting or non-contacting microarrayer, for example. Liquid layer sample applications over unbound substrate molecules would be considered unthinkable, moreover, due to the inevitable cross-contamination such liquid sample layers would engender. As a result, a need remains for a simple, effective and inexpensive peptide or protein array or microarray system which provides an easily fabricated chip using standard microarrayer equipment, which provides a system in which elaborate compensations such as peptide or protein binding, or quenching layers are unnecessary, and to which sample may be simply and easily applied. Also, the need likewise persists for a system which can rapidly deliver small liquid samples to individual reactant positions of an array or microarray without cross-contamination among the reactant positions.

Proteomics and high throughput screening (HTS) are activities that involve the analysis of hundreds to millions of samples. In drug screening, reactions are run in well-plates to produce optical signals (fluorescence, luminescence) indicating that a hit was identified. The search for label-free drug screening could rely on matrix assisted laser desorption/ionization (MALDI) mass spectrometry (MS), which has excellent throughput. However, the reaction constituents then have to be prepared for MS, in a series of steps which are time consuming and expensive and limit the use of MALDI for HTS.

A common approach in proteomics research is to subject a complex protein sample (a cell or tissue lysate) to separation by 2-dimensional gel electrophoresis separation. Positions of high protein concentration, as indicated by dye staining are then removed mechanically as bands or plugs from the gel. The gel containing the sample is crushed to disperse the sample and then subjected to a separation technique to remove the liquid containing the protein solutes. Proteins in the sample can be subjected to chemical cleavage or proteolytic degradation (typically trypsin) to create smaller fragments suited for mass spectrometry. Salt ions are removed from the liquid sample using an ion-exchange resin. The sample is ready for mixing with a MALDI matrix and then delivered by positive displacement liquid handling to a position on a MALDI target. The sample is allowed to dry and is ready for interrogation by mass spectrometry.

U.S. Pat. No. 5,808,300 (Caprioli, "Method and Apparatus for Imaging Biological Samples with MALDI MS") discloses a method of depositing MALDI matrix material on a tissue sample by electrospraying a solution of the matrix onto the sample.

U.S. patent Publication 2002/0195558 discloses the use of acoustic ejection methods to deposit the MALDI matrix material on a tissue sample.

U.S. Pat. No. 6,288,390 (Siuzdak, "Desorption/Ionization of analytes from porous light-absorbing semiconductors") teaches the use of porous semiconductors for matrix-free mass spectrometry to replace conventional MALDI. U.S. Pat. No. 6,288,390 is an alternative technology for analyzing samples without the need for matrix materials.

U.S. Pat. No. 6,569,383 (Nelson, "Bioactive chip mass spectrometry") relies on the capture (binding via biological affinity or chemical linkage) of the analyte to the surface of a target.

Caprioli, R. M., *J. Mass Spectrometry* 38:1081-1092 (2002) discloses a protocol for spraying matrix over a tissue sample by placing ~20 ml of a matrix solution into a glass reagent sprayer (Kontes Glass Company, Vineland N.J. USA) and spraying multiple coats of matrix across the surface of the tissue. No mention is made of the use of this method for drug discovery reactions on a MALDI target, and the disclosed method does not describe use of an ultrasonic nozzle.

Caprioli, R. M., *Electrophoresis* 23, 3125-3135 (2002) describes an aerosol deposition coating method on to tissue. Matrix is air-sprayed on the section using a commercially available glass spray nebulizer connected to a nitrogen bottle (nebulizing glass) to minimize contamination. No mention is made of the use of this method for drug screening reactions.

There is a continued need for improvements in sample processing to high throughput preparation and screening of samples using MALDI MS analysis techniques. Conducting HTS on a MALDI target would meet industry demands for label-free HTS with high capacity (10K to 100K screens per day).

SUMMARY OF THE INVENTION

In order to meet this need, the present invention is a peptide or protein microassay method and apparatus in which a wide variety of chromogenic or fluorogenic peptide or protein substrates of interest are individually suspended or dissolved in a hydrophilic carrier, with aliquots of each substrate being deposited in an array or microarray of reaction loci, or "dots." Each dot, therefore, provides an individual reaction vessel containing the peptide or protein of interest to which a biological sample may be applied for assay purposes. The sample is applied to the array or microarray of dots by one of a variety of focused sample application techniques, including aerosolizing or misting of the sample, or target application of the sample, onto each dot without creating fluid channels between the dots which would cause cross-contamination. In a first embodiment of the present invention, the sample is misted or aerosolized, and the application of such an aerosolized sample to the dots results in the sample's being absorbed by the individual dots while any excess sample droplets between the dots either tend to migrate toward and be absorbed by the nearest dot, or evaporate, leaving each dot as a discrete reaction chamber without fluid reactant connection to any other dot. Known scanning and database creation techniques may be used to analyze reaction indicators present or absent in the arrays of dots.

The present invention provides methods of HTS and preparing samples for MALDI mass spectrometry analysis. Solutes within a solution are analyzed via MALDI with no chemical linkage, immobilization, or adsorption to the surface. Any changes to the solutes (via drug screening reaction, chemical reaction, or enzymatic reaction) occur in the solution phase and do not require linkage of the components to the surface.

The present invention allows HTS reactions to be run directly on a MALDI plate followed by MALDI MS analysis with a detection limit of 1 femtomole of a peptide in 50 nanoliters of sample. Methods of the present invention employ the power of contact pin printers to load MALDI plates at up to 1000 drops per square centimeter. Using the methods of the present invention, MALDI matrix can be applied with high quality such that ultrasmall liquid samples can be used while still generating outstanding crystals for the MALDI process to allow ultrasensitive detection.

The methods of the present invention provide the ability to run individual nanoliter to microliter volume liquid reactions at positions on a mass spectrometry (MS) target plate. The target is a non-porous metal surface that is flat or has wells, coatings, grooves or other means to maintain sample position. Reagents are added to each sample position by various liquid handling protocols to initiate reactions. The constituents and products of each reaction are then prepared for MALDI mass spectrometry analysis by drying and deposition of the MALDI matrix, without the need for removal of the sample from the MS target for various manipulations, such as desalting, extraction, solvent exchange, digestion, MALDI matrix addition and formation. These methods can be used for reaction optimization, high throughput drug discovery, high throughput drug selectivity profiling or toxicity testing.

More specifically, the present invention provides a method of transferring molecules of interest from an electrophoretic polymer gel to a MALDI target plate comprising the steps of:
(i) providing an electrophoretic gel containing one or more molecules of interest;
(ii) replacing water within the electrophoretic gel with a cosolvent mixture;
(iii) positioning a pin over the gel and penetrating the gel with the pin;
(iv) energizing the pin to deplete the gel in a region surrounding the one or more molecules of interest, causing the cosolvent mixture to surround the one or more molecules of interest;
(v) lifting the pin out of the gel, the pin carrying a drop of the cosolvent mixture containing the one or more molecules of interest; and
(vi) contacting a MALDI target plate with the pin, the contacting causing the drop of cosolvent mixture containing the one or more molecules of interest to be deposited on the MALDI target plate.

In a further aspect, the present invention provides a method of running chemical reactions on a MALDI target plate comprising: depositing drops of reactants on the target plate; depositing a reagent on the target plate such that the reagent contacts the deposited drops; and allowing the chemical reaction to proceed.

In yet a further aspect, the present invention provides a method of preparing a sample for MALDI mass spectrometry analysis comprising the steps of:
(i) providing a target plate having liquid drops of sample;
(ii) drying the target plate to remove solvents from the sample drops;
(iii) depositing a MALDI matrix onto the dry target plate;
(iv) humidifying the target plate; and
(v) subjecting the target plate to MALDI mass spectrometry for analysis of the sample drops.

In an additional aspect, the present invention provides a method of depositing one ore more layers of a MALDI matrix on a target plate comprising:
(i) providing a target plate having samples thereon;
(ii) aerosolizing the matrix; and
(iii) spraying the aerosolized matrix on the target plate while moving the target plate.

BRIEF DESCRIPTION OF THE DRAWING(S)

Figure 1:
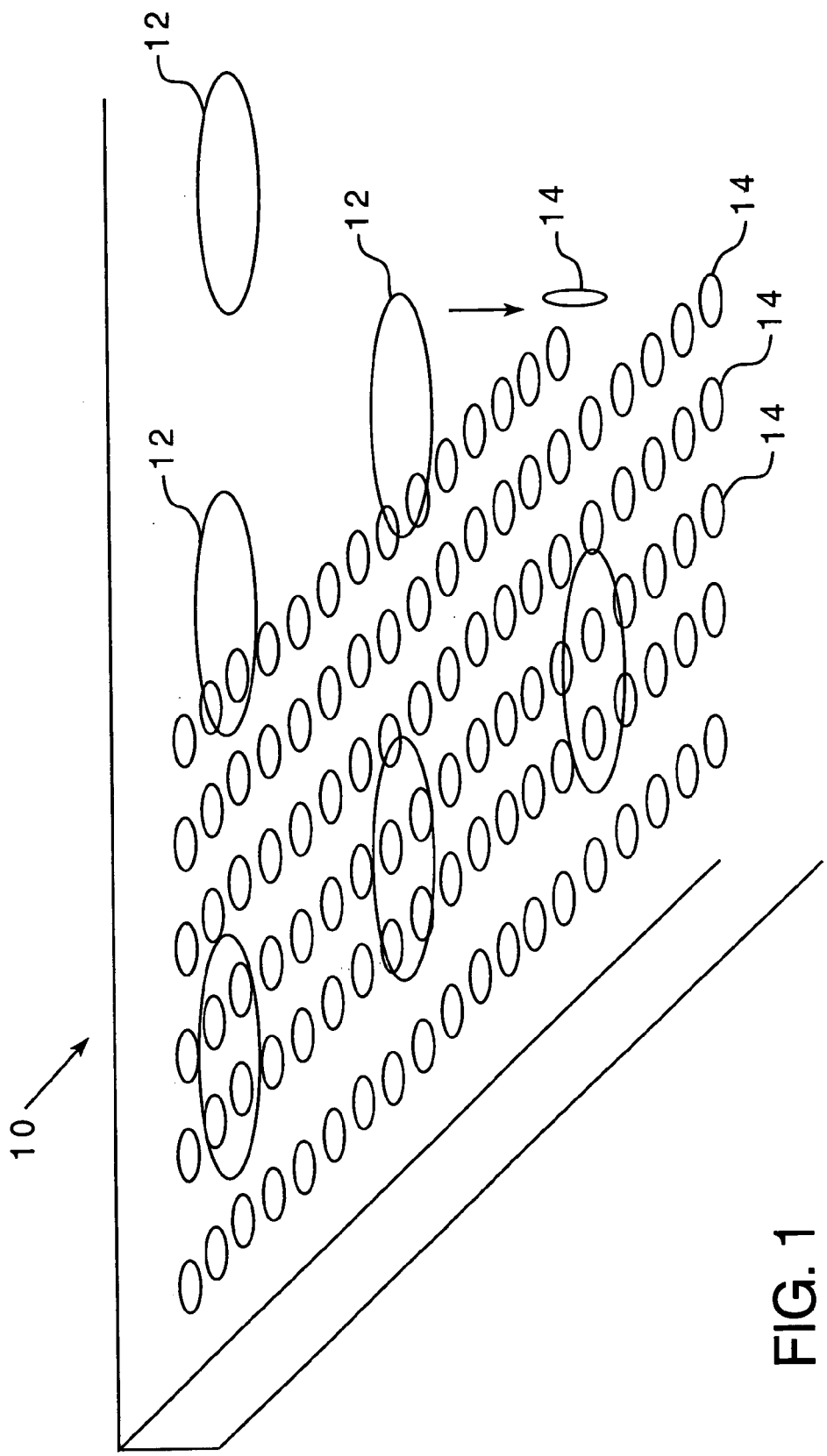
Figure 4:
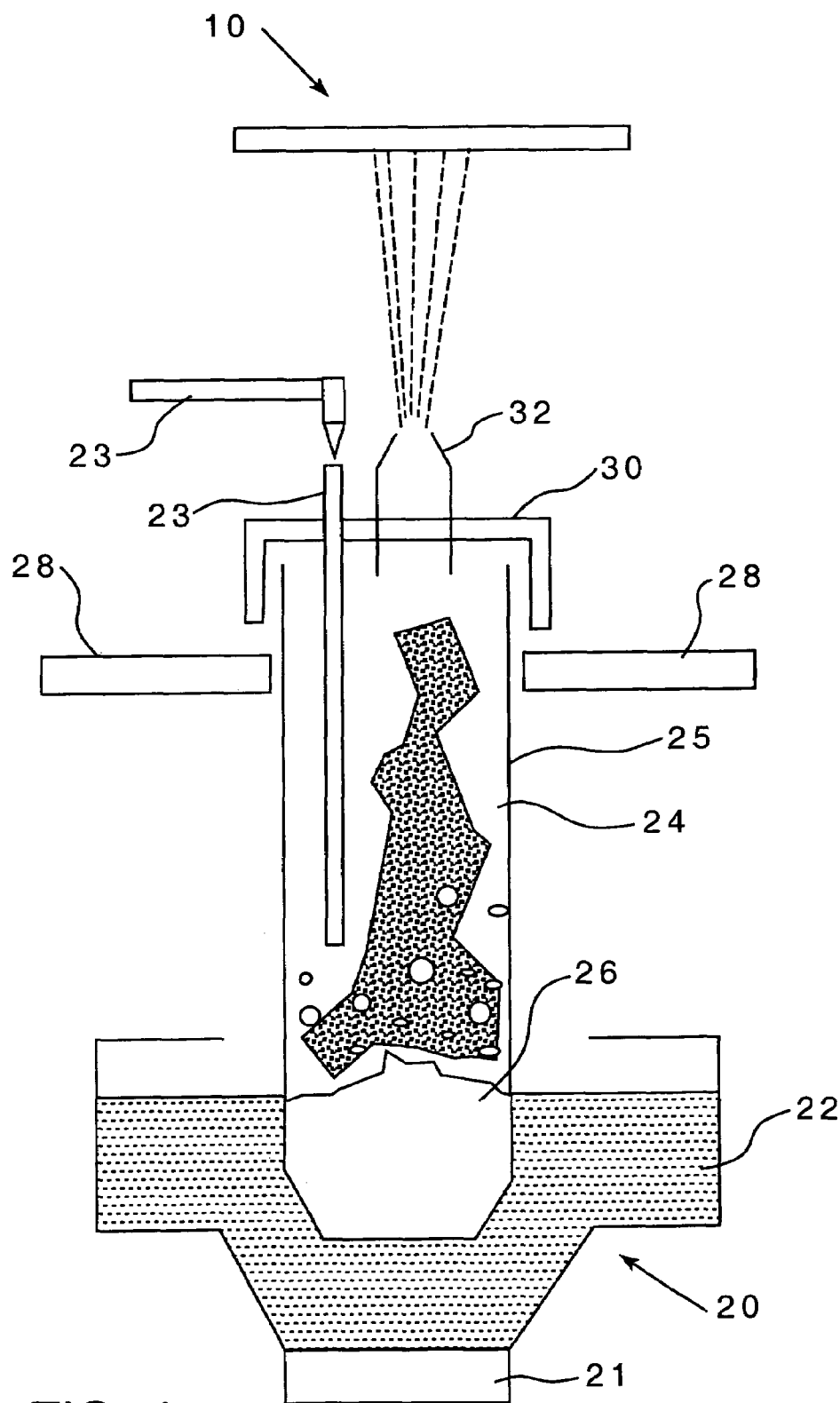
Figure 5:
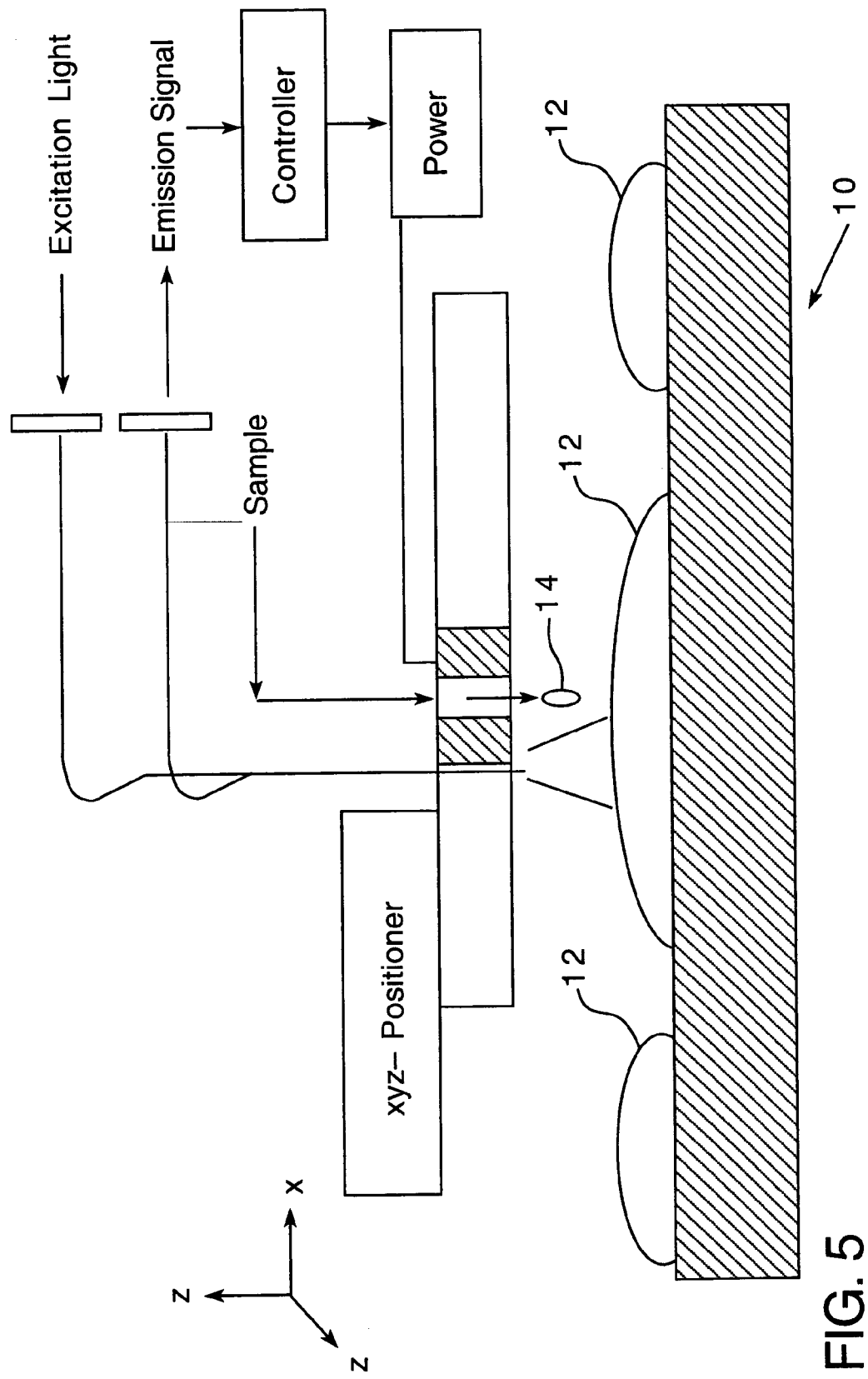
Figure 6:
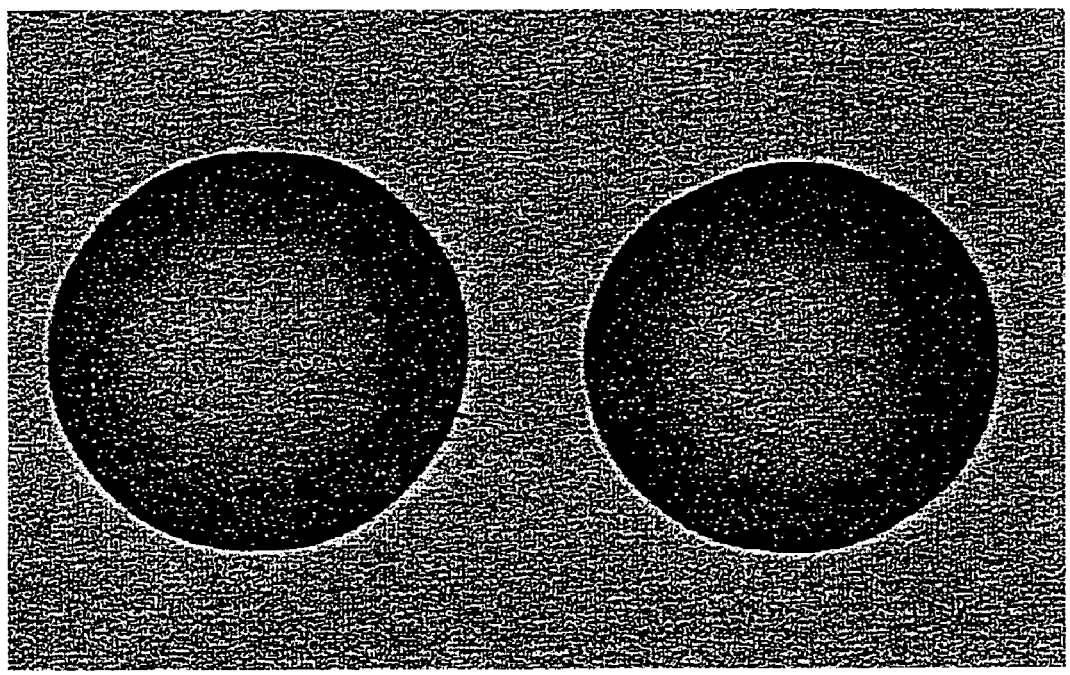
Figure 7:
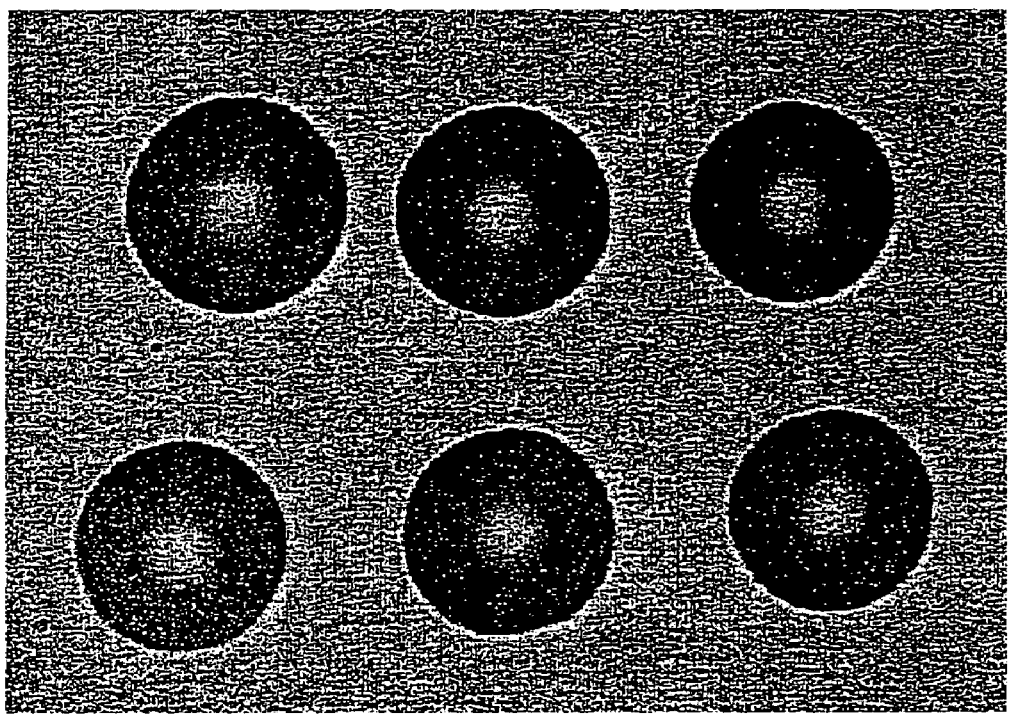
Figure 8:
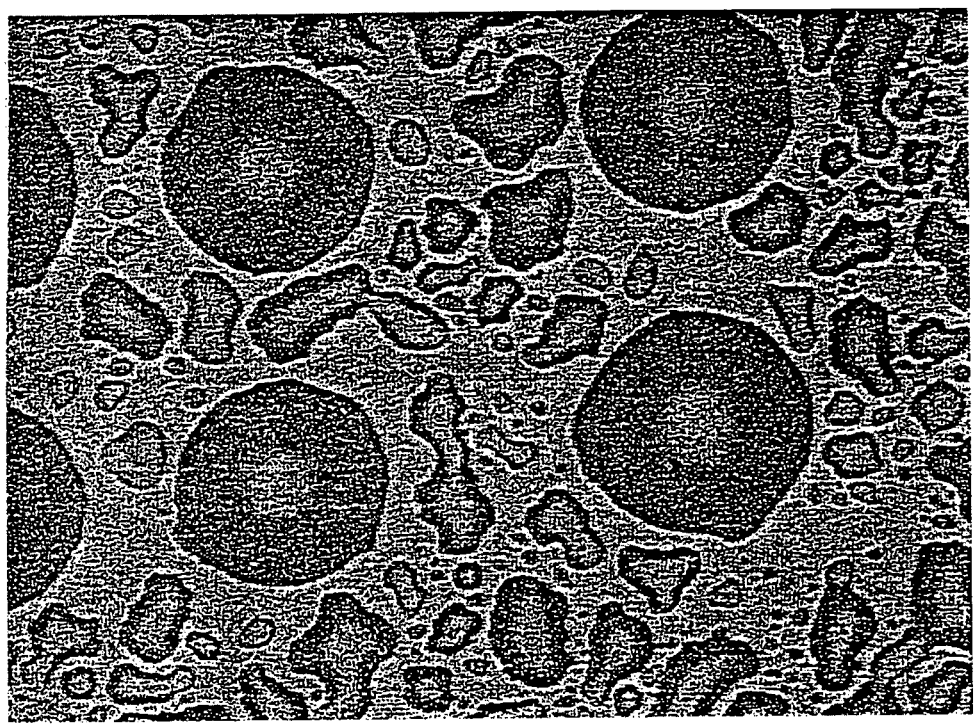
Figure 9:
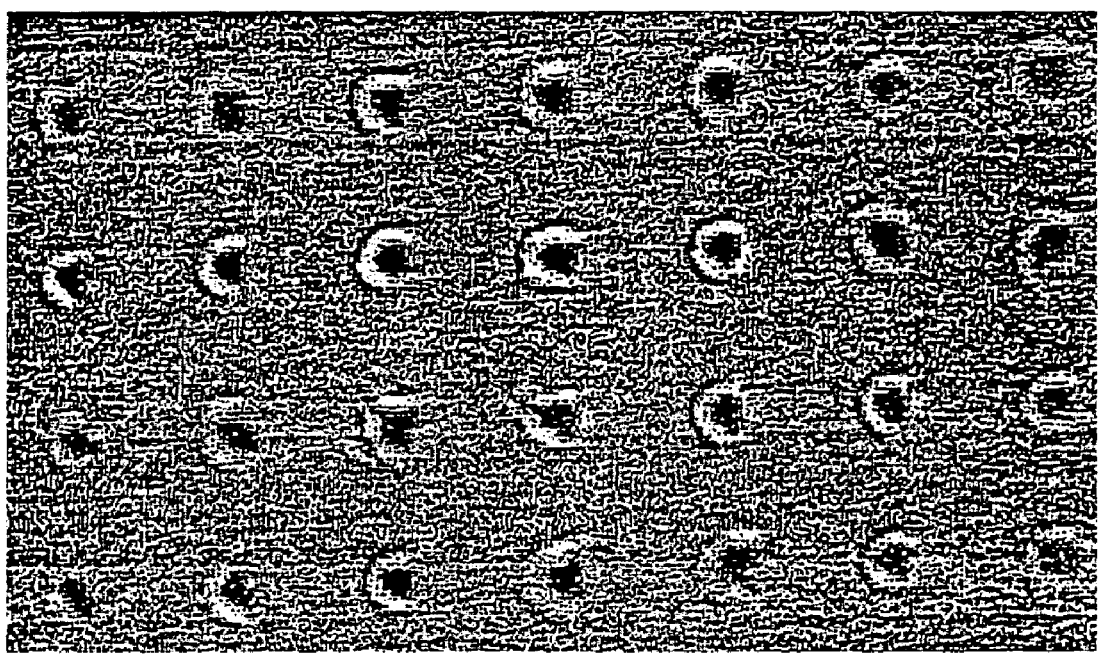
Figure 10:
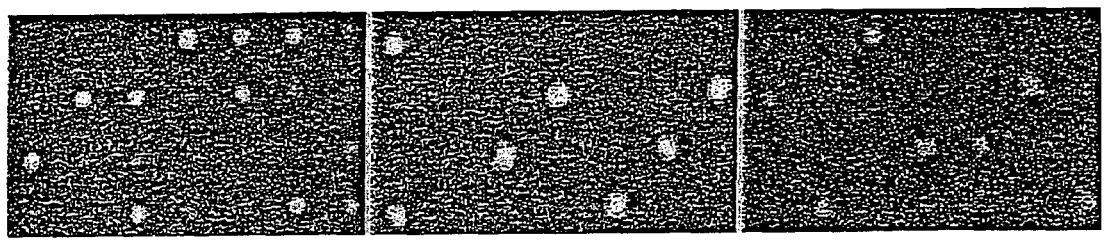
Figure 11:
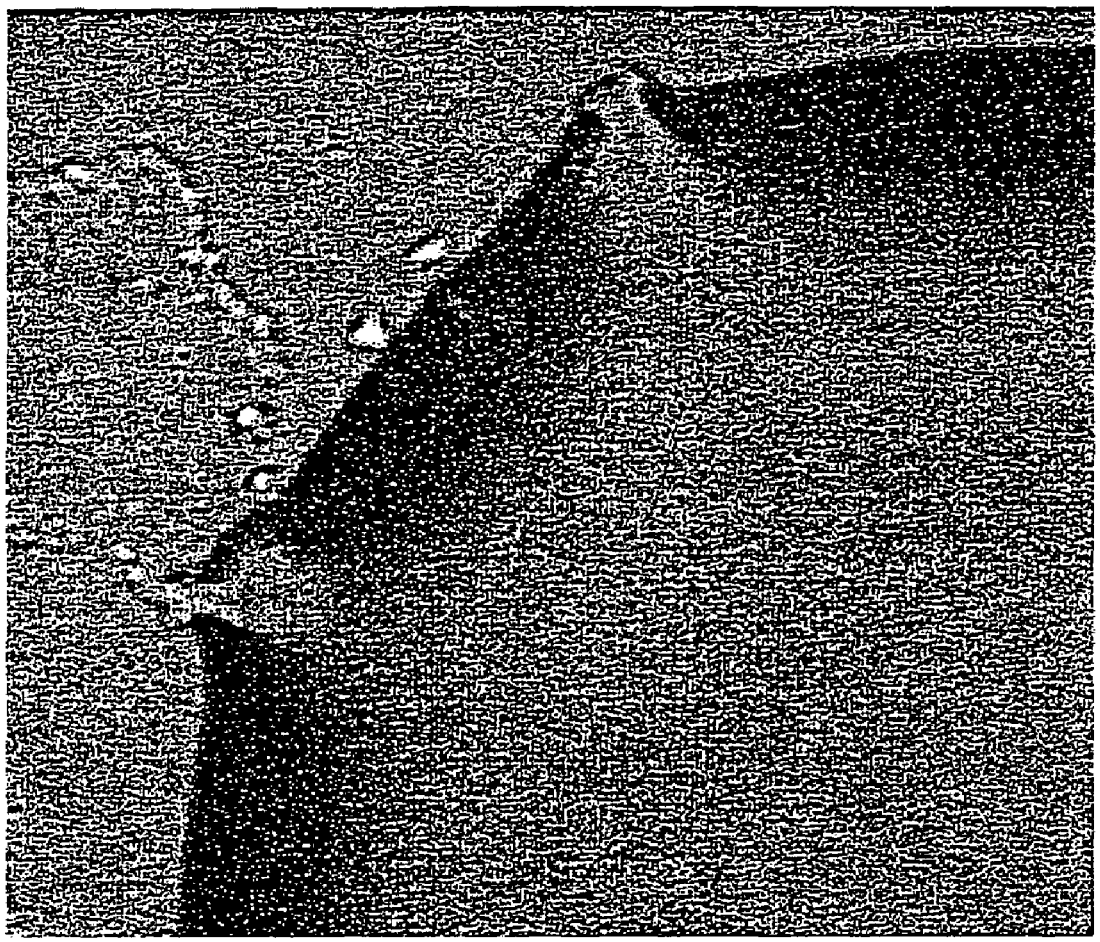
Figure 12:
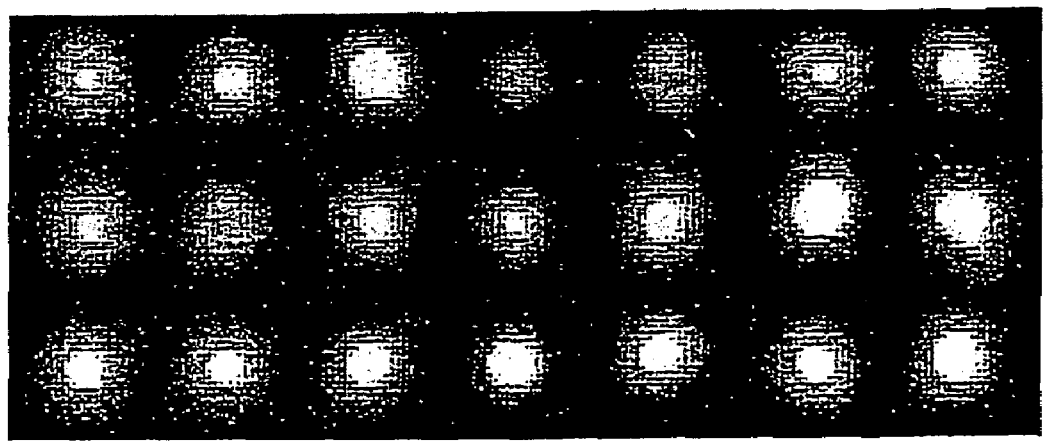
Figures 13A, 13B, 13C, 13D:
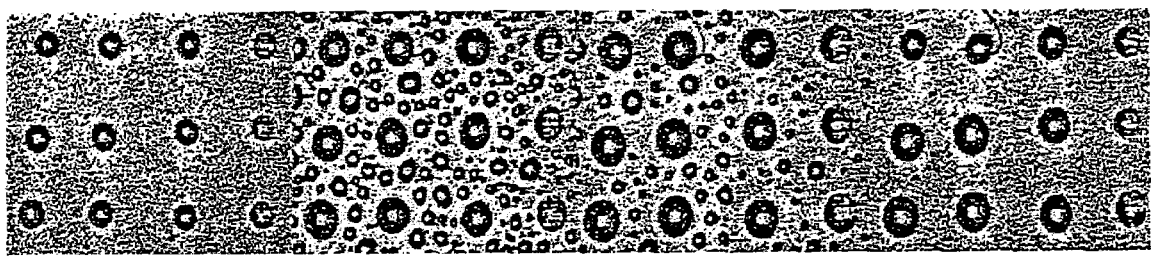
Figure 14:
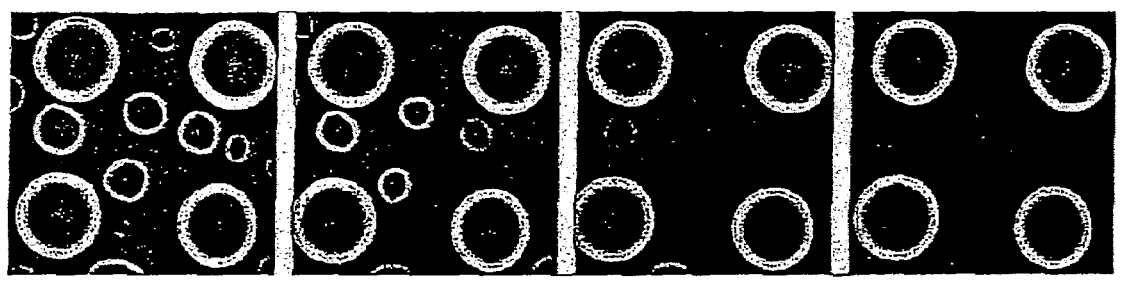
Figure 15:
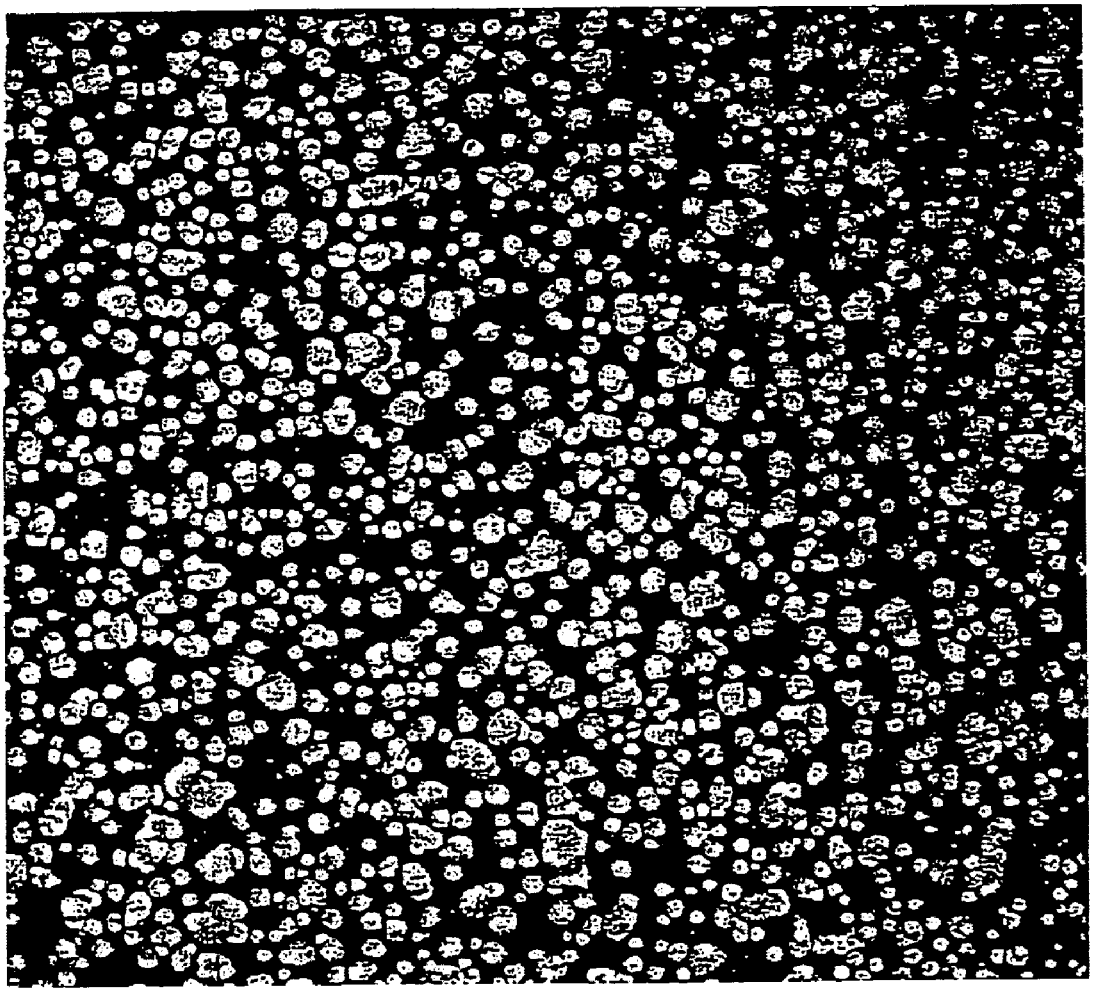
Figure 16:
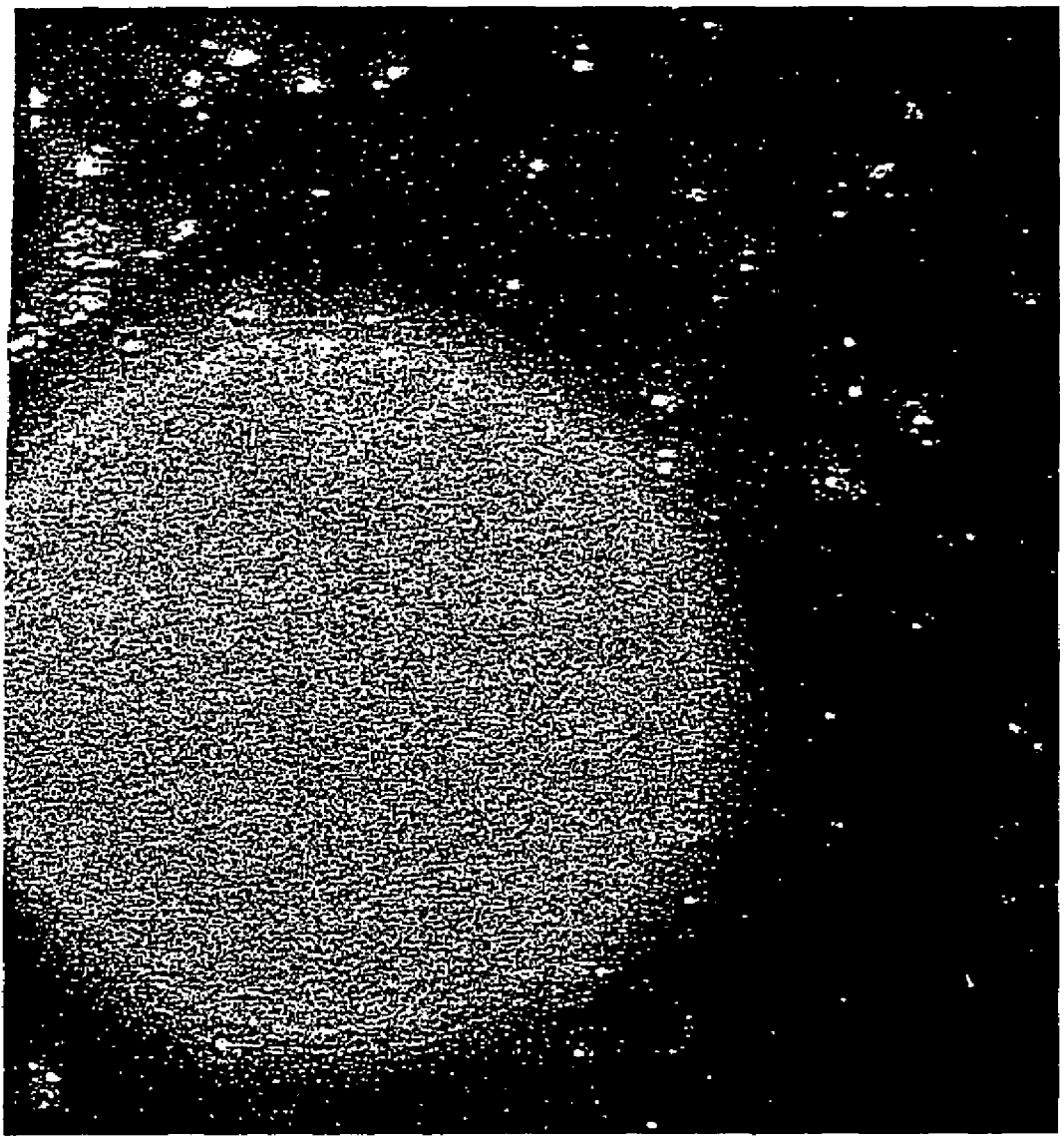
Figure 17:
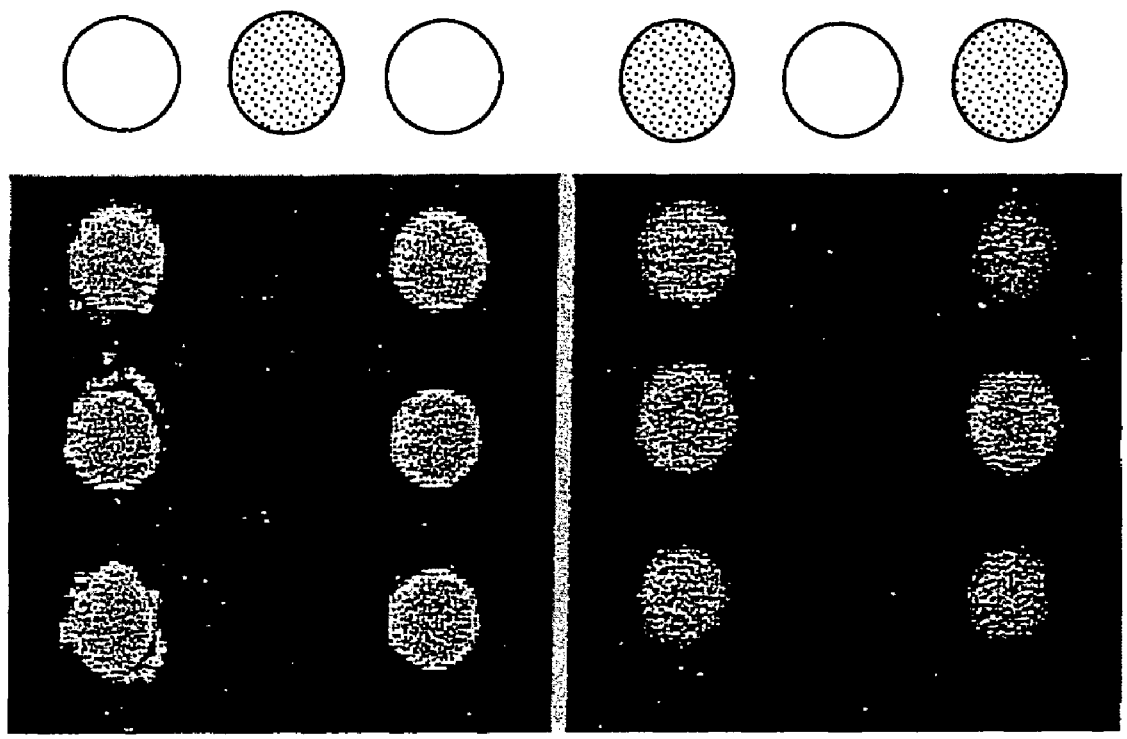
Figure 18:
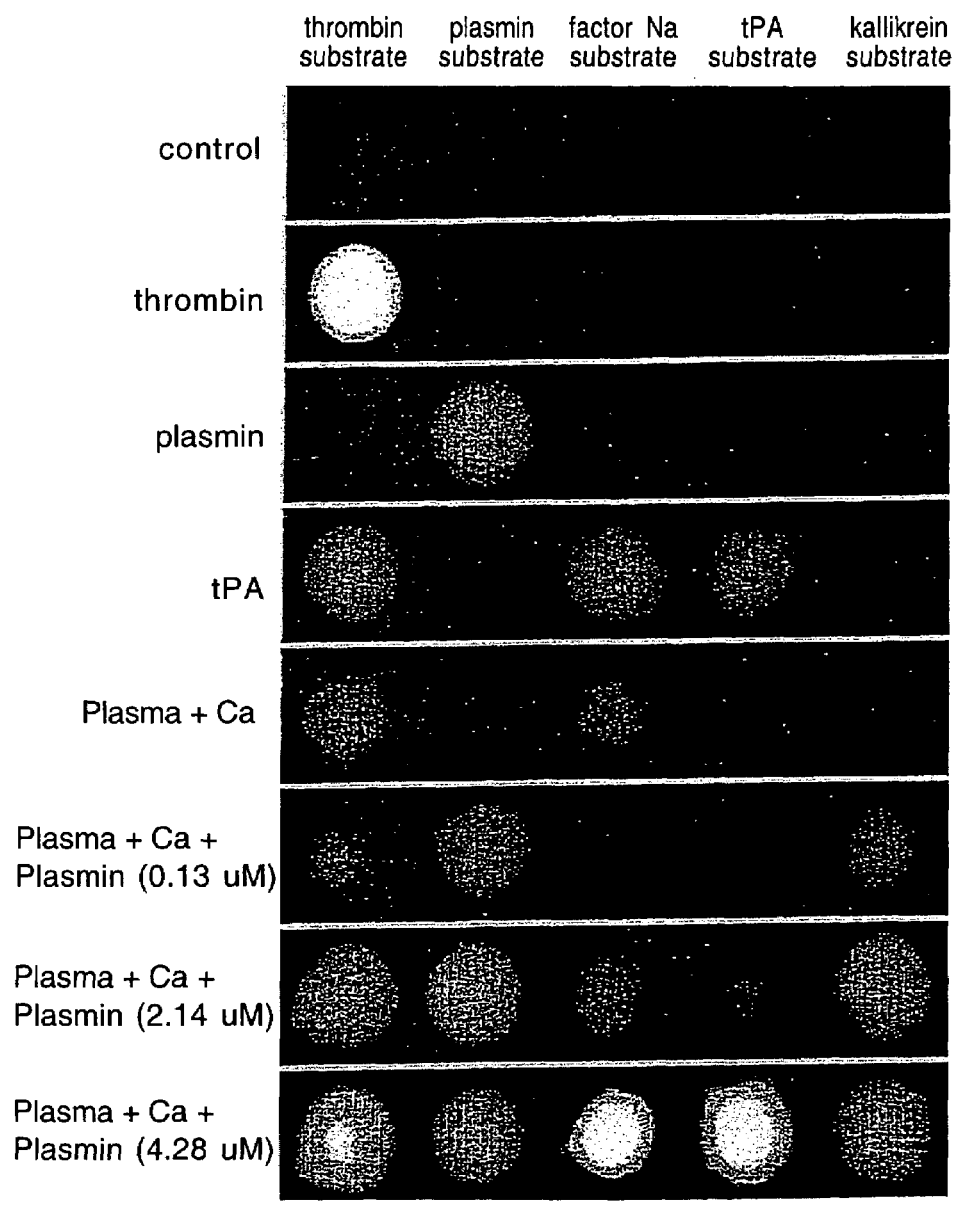
Figure 19:
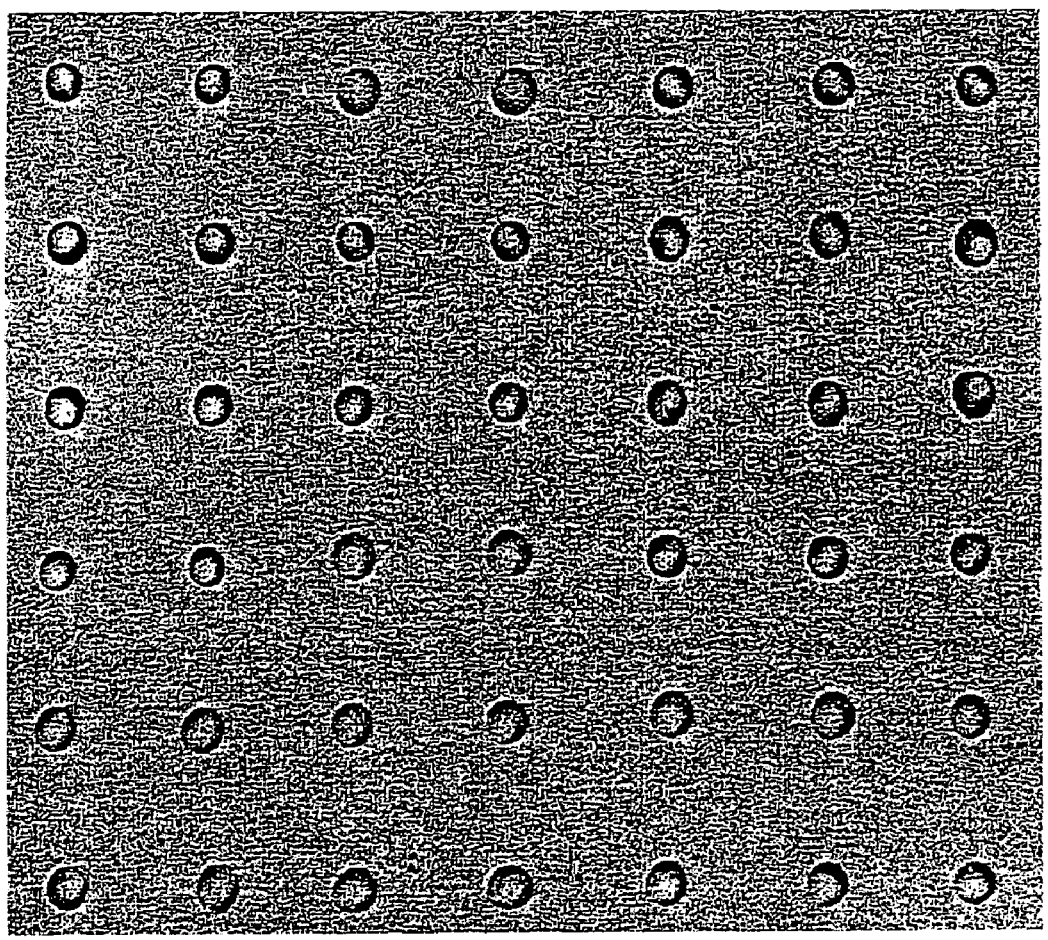
Figure 20:
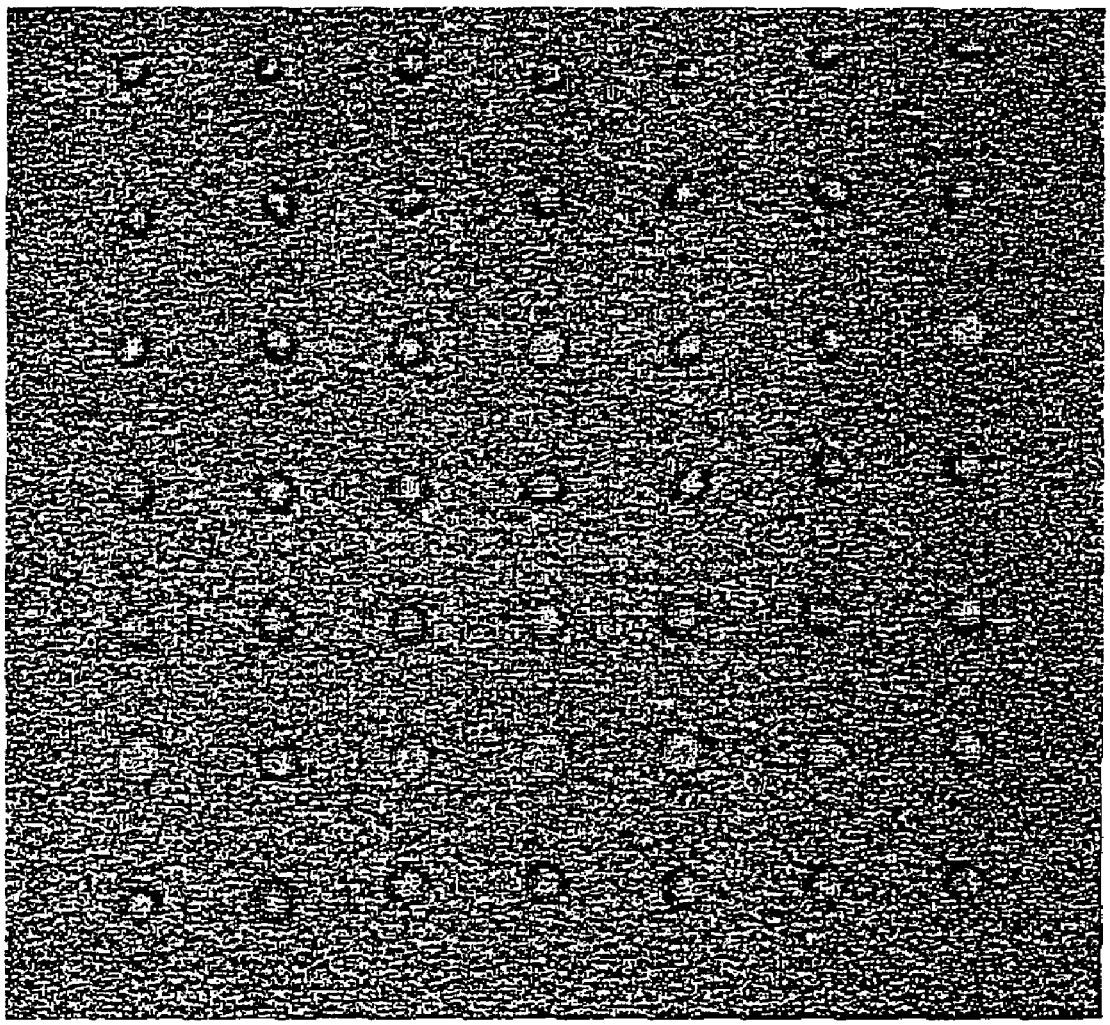
Figure 21:
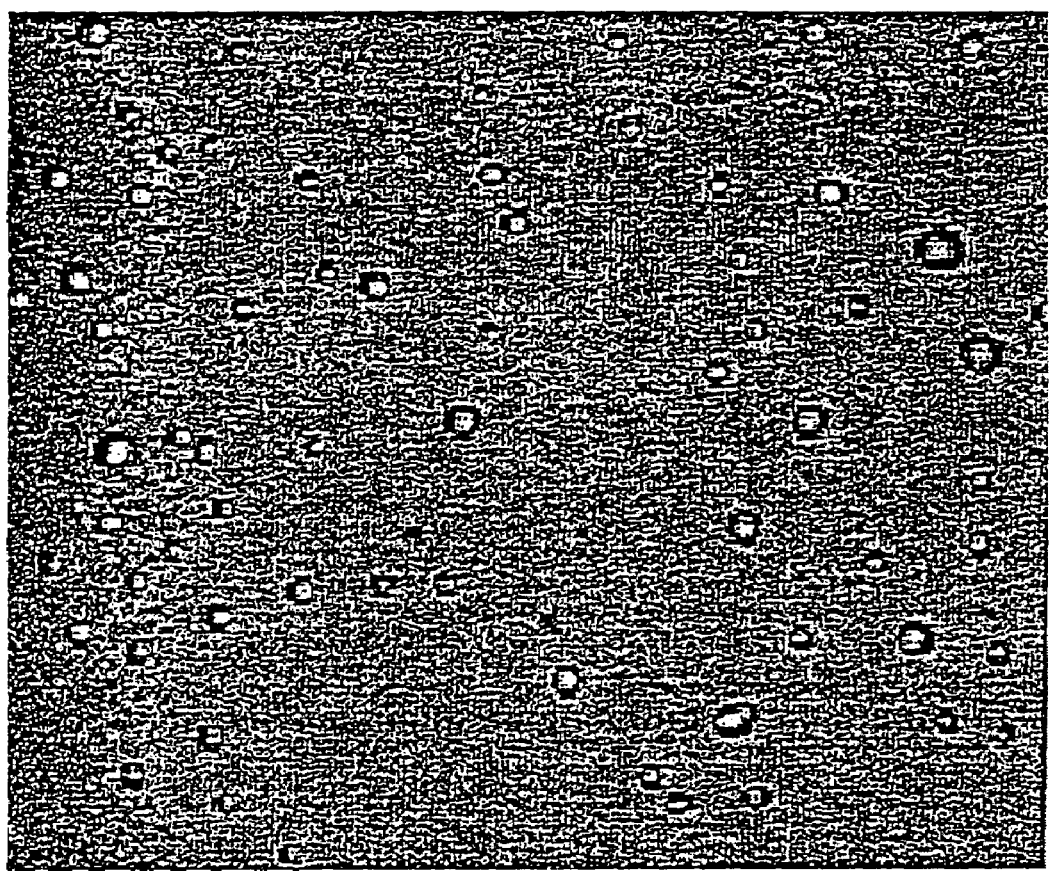
Figure 22:
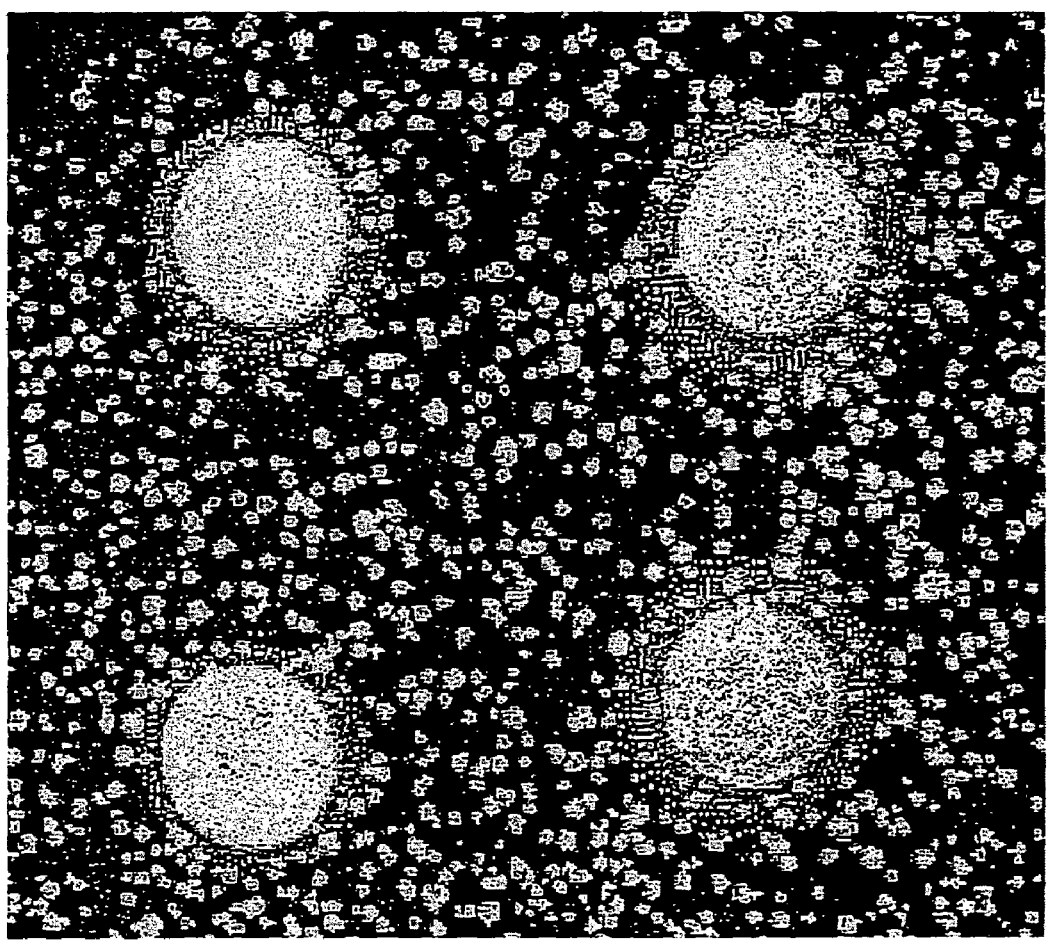
Figure 23:
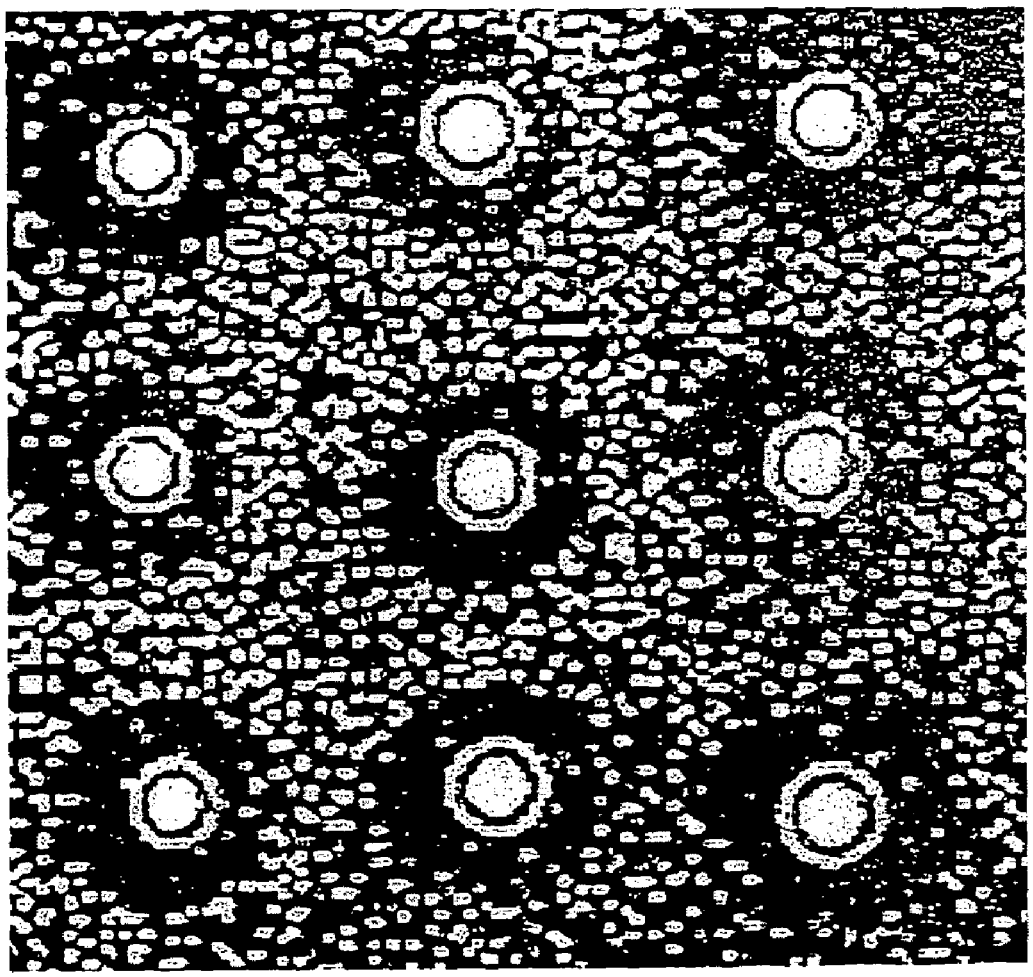
Figure 24:
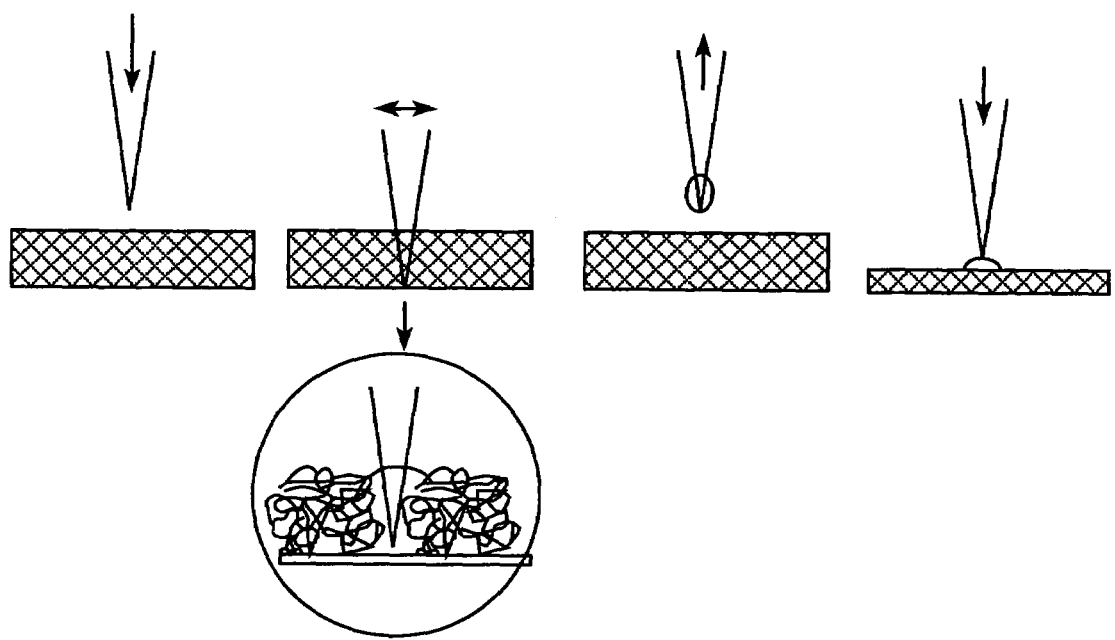
Figure 25:
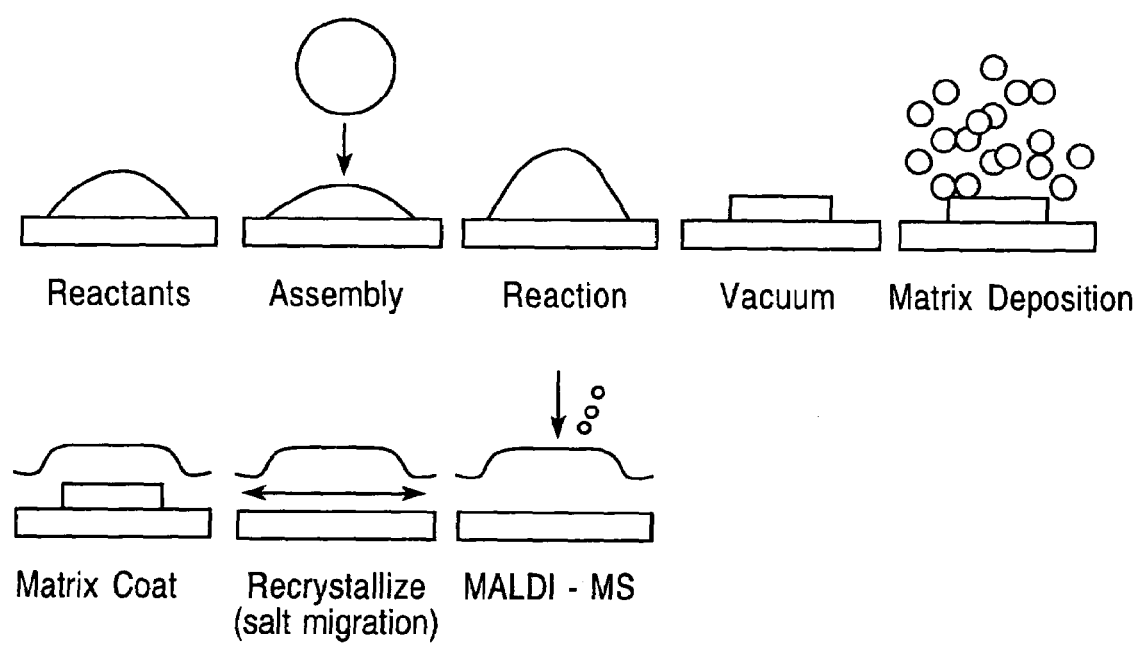
Figures 26A, 26B:
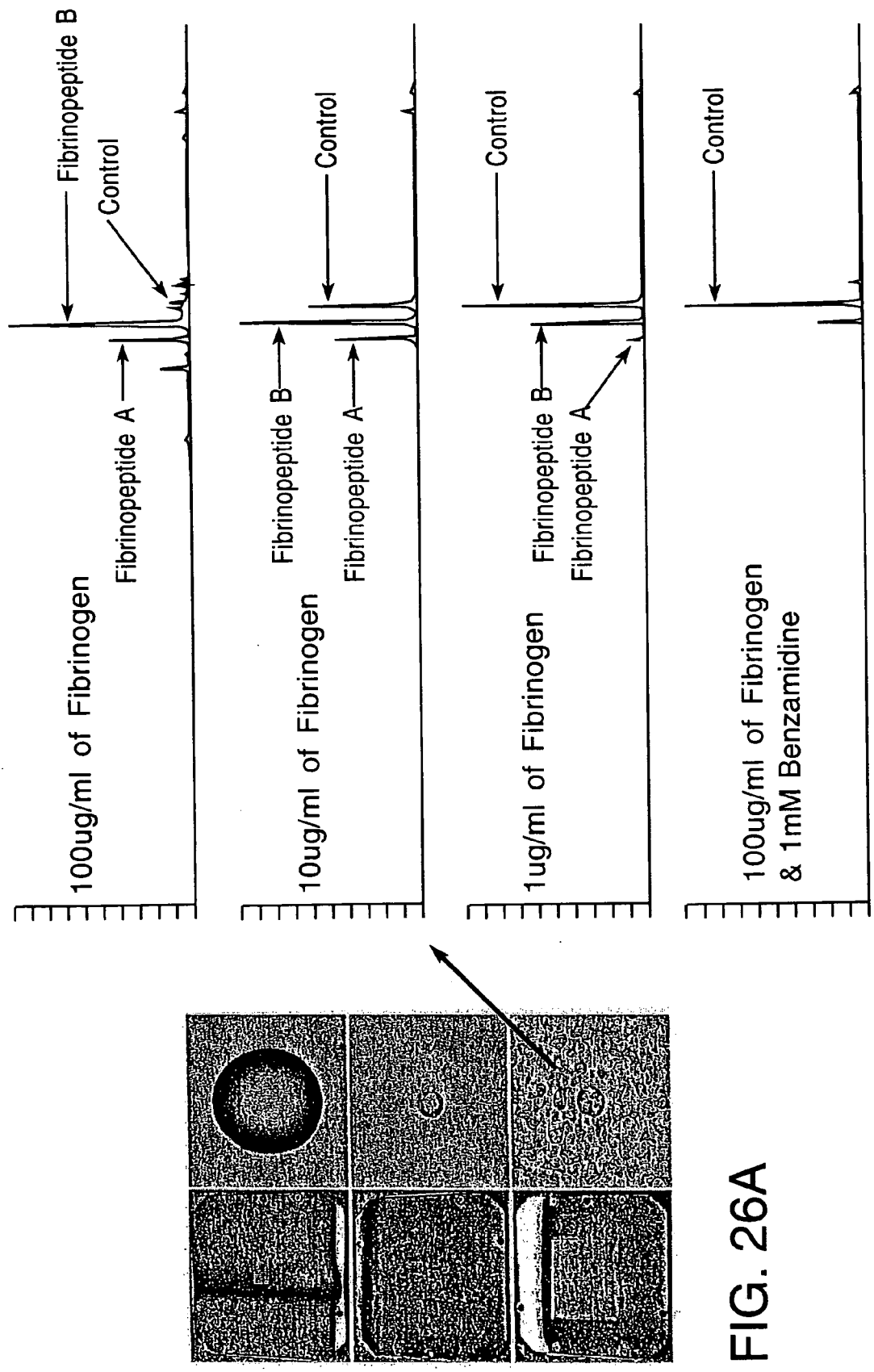
Figure 27O:
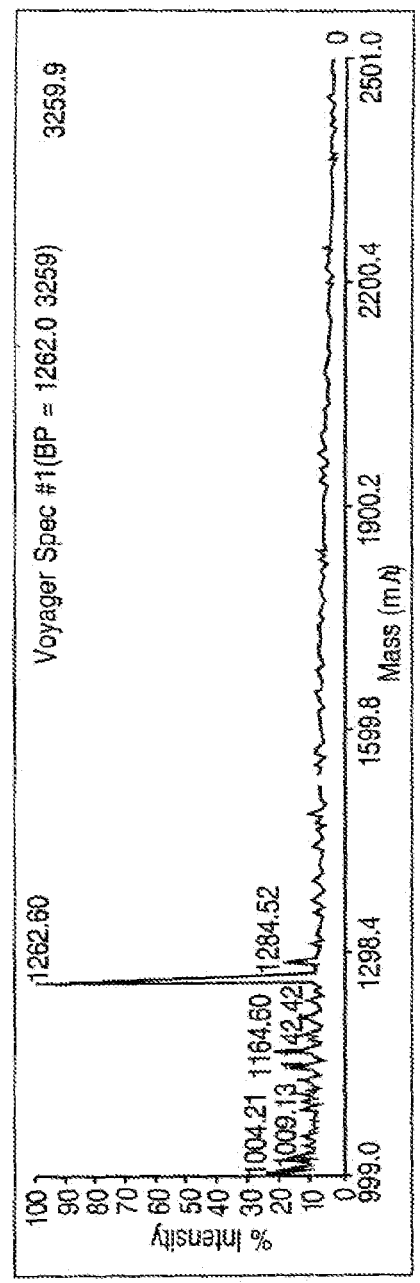

FIG. 1 is a partial perspective view of an array according to the present invention;
FIGS. 2A, 2B and 2C are side elevational views of arraying, aerosol sample deposition and substrate conversion, respectively;
FIGS. 3A and 3B are schematic diagrams of peptide or protein microarrays before and after sample application;
FIG. 4 is a sectional view of an ultrasonic misting device;
FIG. 5 is a functional diagram of the assay apparatus;
FIG. 6 is an array of carrier solvent (glycerol) microdots;
FIG. 7 is a prespray array of carrier solvent (glycerol) microdots;
FIG. 8 is an array of microdots sprayed with water-based sample;
FIG. 9 is a proximal view of a sprayed microdot array after mist evaporation;
FIG. 10 is an activated microdot array;
FIG. 11 shows fusion of water droplets containing sample with glycerol microdot;
FIG. 12 shows detection of thrombin activity by microdot assay;
FIGS. 13A, 13B, 13C, and 13D show microfluidics technology for reagent delivery to individual reaction compartments;
FIG. 14 shows delivery of molecules to reaction spots using spray generated from an ultrasonic nozzle;
FIG. 15 shows generation of ultrafine mist using ultrasound transducer and non-contacting chamber;
FIG. 16 shows delivery of molecules to reactive spots using small droplet spray generated by an ultrasound transducer and non-contacting chamber;
FIG. 17 shows that adjacent reaction spots do not cross-contaminate after spray delivery of mist;
FIG. 18 shows a microarray assay of purified enzymes and human plasma;
FIG. 19 is a microarray of caspase substrate;
FIG. 20 is an activated caspase microarray;
FIG. 21 shows mist delivered by an assay system;
FIG. 22 shows fluorescent mist delivered to microarray; and
FIG. 23 shows capture of mist on microarray using an electrostatic charge.
FIG. 24 is a schematic diagram illustrating a method transferring molecules of interest from an electrophoretic gel to a MALDI target plate.
FIG. 25 is a schematic diagram illustrating methods of running chemical reactions directly on a target plate and then preparing the target plate for MALDI mass spectrometry analysis.
FIGS. 26A-B are computer-generated drawings and mass spectrum data obtained from the analysis as described in Example 10.
FIGS. 27A-O are mass spectrum data obtained from the analysis as described in Example 11.

DESCRIPTION OF THE PREFERRED EMBODIMENT(S)

The present invention is a peptide or protein microassay method and apparatus in which a wide variety of chromogenic or fluorogenic peptide or protein substrates of interest are individually suspended or dissolved in a hydrophilic carrier, with aliquots of each substrate being deposited in an array or microarray of reaction loci, or "dots." Each dot, therefore, provides an individual reaction vessel containing the peptide or protein of interest to which a biological sample may be applied for assay purposes. The sample is applied to the array or microarray of dots by one of a variety of focussed sample application techniques, including aerosolizing or misting of the sample, or target application of the sample, onto each dot without creating fluid channels between the dots which would cause cross-contamination. In a first embodiment of the present invention, the sample is misted or aerosolized, and the application of such an aerosolized sample to the dots results in the sample's being absorbed by the individual dots while any excess sample droplets between the dots either tend to migrate toward and be absorbed by the nearest dot, or evaporate, leaving each dot as a discrete reaction chamber without fluid connection to any other dot. Known scanning and database creation techniques may be used to analyze reaction indicia present or absent in the arrays of dots.

Generally, this invention can be applied to areas of biotechnology and biomedicinal research. More specifically, this invention can be used to study enzyme activities, as well as cofactors, inhibitors and activators of enzymes. In one application, the assay may be used in drug research, namely drug discovery, by screening the effect of large combinatorial libraries of compounds on activities of generally between ten up to thousands of enzymes, or drug interaction in blood chemistry, matrix metalloproteases, angiogenesis, tyrosine phosphoprotein phosphatases, or apoptosis regulation. The assay can be applied to genomics or proteomics research, in particular, epigenetic regulation of enzyme systems. In a further application, the assay can be used to research signal transduction pathways, such as kinase and phosphatases in gene regulation. The assay may also be used for structural and functional research of combinatorial studies involving point mutations on enzyme substrate specificity. The assay may be applied to blood research, namely, coagulation diagnostics and thrombolytic research, or the assay can be applied to viral research and diagnostics of viral proteases and processing activities. The assay can thus be employed throughout various fields of biological research due to its simplicity and versatility. As mentioned above, the assay is suitable for use with existing scanning technologies in place for genomic studies.

In the above and ensuing description, the following terms may be understood as follows. A reaction loci is generally an adherent non-spreading volume of fluid on a solid surface. A reaction spot can be referred to as "spot", "dot", "reaction zone", "reaction center", "microdot", or "microassay." A chip is a planar surface containing non-spreading reaction dots. Chips can also be referred to as a "glass slide", "slide", "surface", "solid substrate", "bioreaction microarray", "bioreaction chip", and "bioreaction slide." Spray refers to the delivery of an aerosol of liquid sample to a solid surface containing reaction spots. Spray can also be referred to as a "mist", "aerosol", "atomized mist", "droplet/s" or "nebulized mist."

The present assay generally comprises microreactions in a liquid phase which are created by applying small volumes of a fluid mixture of a peptide or protein substrate, a hydrophilic carrier solvent and a volatile solvent to a nonporous surface, whereby evaporation of the volatile solvent results in highly localized long-lasting liquid or semi-solid dot or microdot residues of substrate in a hydrophilic carrier solvent. The substrate is fluorogenic or chromogenic to enable analysis of the reaction, if any, within the hydrophilic carrier after the sample is applied. The nonporous surfaces for delivery of the fluid mixture can include silicon, glass, silica, quartz, polystyrene or other nonporous polymeric membranes. Overall, the components of the assay are usually combined and applied via a computer-controlled application system, and microreactions are monitored via a computer-based scanning and database producing system.

Particularly, when the arrays involved are microarrays, the presence of the volatile solvent facilitates fluid creation of the microdot by reducing the overall viscosity of the formative fluid admixture. The volatile solvent generally has the ability to evaporate and suitable volatile solvents include, without limitation, dimethylsulfoxide (DMSO); chloroform; acetone; acetic acid; water; an alcohol such as methanol, ethanol or propanol; ethyl ether or alkane. After application of the fluid admixture to a nonporous surface, the volatile solvent evaporates, leaving microdots containing hydrophilic carrier solvent and the suspended or dissolved chromogenic or fluorogenic substrate(s). These constituents remain in a liquid or semi-solid state without crystallization or precipitation of the substrate(s).

At the time of a sample application, the hydrophilic carrier suspends or dissolves the substrate(s) to maximize the bioreaction potential with later applied biological samples. The hydrophilic carrier generally possesses the following characteristics: miscibility with the volatile solvent; miscibility with water; miscibility with aqueous biological fluids; suitability for maintaining a stable solution or suspension of fluorogenic or chromogenic substrate(s) at high concentrations; moderate viscosity between 1 centipoise and 10,000 centipoise; compatibility with biological molecules such as nucleic acids, peptides, proteins, and sugars; suitable fluidity for movement into and out of microcapillary devices such as the hollow tips of microarray pins or microsyringes used for arraying; a specific contact angle sufficient to form a stable finite lens where the bioreaction fluid in the spot after arraying does not spread (contact angle >0 is required); a specific contact angle low enough to form a stable adherent lens that does not have too low of adhesion such that the spot has limited adhesion and can roll on the substrate (contact angle <90 is required); and low volatility such that the reaction zone does not evaporate. Glycerol 1,2,3-propanetriol) is an example of such a fluid that possesses all of these characteristics. Other examples of the hydrophilic carrier solvent include a polyalcohol such as 1,2-ethanediol or 2,3-butanediol. In addition, the carrier solvent may contain viscosity enhancers such as dextran, pluronic acid, carbohydrates of the pentose, ribose or hexose families or related polysaccharides or polyethylene glycol polymers.

The microdots are generally applied to the nonporous surface in a microarray configuration. The final volume of the microdot, after evaporation of the volatile solvent, ranges from about 1 nL for a 10 μm diameter microdot to about 1 to 10 nL for a 100 μm dot. Microdots can be applied through fluid handling methods of direct positive displacement pumping. Alternatively, the microdot is applied through "arraying", whereby computer controlled metal, glass or plastic tips pick up droplets of fluid from a reservoir by capillary action and make contact with the solid surface, or by laser printing or jet printing techniques. Arraying is accomplished by using well-established pin technologies (i.e., Telechem Pins, GeneMachine arrayer). The separation distance between microdots ranges from 50 to 1000 μm. Delivery of 1 to 10 nL of formulation is sufficient to create a microdot.

After creating a high density array of microdots, each of which contains a specific fluorogenic or chromogenic reporter substrate, as well as other possible reaction modifiers, a small sample of biological fluid is applied to the microdots. Each microdot is inoculated with sample by application of the biological fluid, generally through deposition of a fine mist on the biochip. The mist is applied in a manner that does not form a wetting film and never bridges two adjacent glycerol droplets. In other words, the application of the aerosolized sample to the dots results in the sample's being absorbed by the individual dots while any excess sample droplets between the dots either tend to migrate toward and be absorbed by the nearest dot, or evaporate, leaving each dot as a discrete reaction chamber without fluid reactant connection to any other dot. Delivery of the biological fluid containing a corresponding relevant enzyme will cause reaction and concomitant activation of the chromogenic or fluorogenic substrate in each glycerol droplet. In other words, enzyme or chemical constituents of the biological fluid lead to the activation or antagonism of the activation of the fluorogenic substrate in the microdot to produce a fluorogenic or chromogenic signal readable by epifluorescence or confocal scanning, direct imaging or light absorption. An individual chip can be configured to report the activity of numerous proteases, kinases, phosphatases, oxidoreductases, lipases and inhibitors or activators of these enzymes, each within an individual dot or microdot loci of each reaction of interest.

It should be borne in mind that the present peptide and protein chips are considerably simpler than most if not all prior art arrangements which include means for physically adsorbing or binding peptides or proteins directly to the glass slide or chip, or which contain multiple components including but not limited to quenching overlayers, gel pads or other features more complex than the present reaction loci. Constituents inconsistent with the practice of the present invention would be anything which would interfere with the hydrophilic carrier's providing a discrete reaction vessel containing the peptide or protein of interest and any other constituents designed to facilitate sample absorption, reaction and reaction detection.

The invention is further illustrated in the accompanying FIGS. 1-5.

Referring now to FIG. 1, a biochip 10 has arrayed thereon a plurality of reaction loci 12, over which are applied the aerosolized or misted or ink-jet printed sample droplets 14. The vertical arrow illustrates vertical deposition of the sample droplets 14.

FIGS. 2A, 2B and 2C are side elevational views of arraying, aerosol sample deposition and substrate conversion, respectively, according to the present invention. In FIG. 2A, a microarrayer tip 16 is shown depositing the reaction loci 12 onto the biochip 10. In FIG. 2B, the aerosolized or misted sample droplets 14 are shown in the process of deposition onto the reaction loci 12. In FIG. 2C, the sample droplets 14 have either absorbed into the reaction loci 12 or have evaporated and disappeared completely from the biochip 10. In FIG. 2C, individual reaction loci 12 can generate color or fluorescence as a result of substrate conversion.

FIG. 3A is a schematic diagram showing a blanket sample application over all the reaction loci 12 of the biochip 10 in a square or rectangular pattern 18, whereas the reactant of FIG. 3B reposes solely within the confines of the reaction loci 12 of the biochip 10. The result shown in FIG. 3B can occur through various mechanisms including but not limited to the blanket sample application may be of an aerosol or mist which evaporates from between the reaction loci 12; or the sample may be targeted for application to the reaction loci 12, such as by a laser printer or ink-jet printer; or the sample may be applied through a mask or template which blocks sample application from any area other than the reaction loci 12.

FIG. 4 illustrates, in section, a nebulizer 20 containing an ultrasonic generator (transducer) 21 filled with a liquid 22 adapted to receive a container 25 having a sample 26 therein, whereupon energization of the sample 26 by the transducer 21, the aerosol mist made from the sample 26 may exit the nozzle 32 for deposition on the biochip 10. Optionally, a carrier gas 24 enters the container via inlet 23, which carrier gas 24 helps to displace the aerosolized sample 26 for deposition onto the biochip 10. For the purpose of FIG. 4, it should be borne in mind that the biochip 10 is inverted compared to the biochip position shown in the remaining Figures. The nebulizer 20 also contains optional placement guides 28 for holding the container 25 in position, as well as a cap 30 for the container 25 through which the nozzle 32 extends as shown.

FIG. 5 is a schematic illustrating the juxtaposition of various components of the present assay system as positioned adjacent the biochip 10, the reaction loci 12 and the sample droplet(s) 14. These components may include, without limitation, a printhead for sample application, an xyz positioner, a power supply, a controller, and means for providing excitation light and detecting emission signal, among other components. More particularly, major components of the assay system (apparatus) include a set of operating instructions resident in computer software that sends via serial or parallel port signals to start, to stop, to establish operating set point, and to control the subcomponents of the assay device, whereby each subcomponent may have an internal or external standing controller or driver. The subcomponents of the device include the following: multiple positive displacement microsyringe pumps; aerosol generating devices, such as pressure nozzles, ultrasonic nozzles, ink-jet printheads, position-actuated ink-jet printheads, surface-actuated ink-jet printheads, fluid contacting or fluid non-contacting ultrasonic transducers; gas flow meter/controller; xy positioner system; and an exhaust/filtration fan.

Aerosolized sample application may be facilitated through the use of computer controlled microsyringes. The computer controlled microsyringes are used for timed sample delivery at constant low rate, and each positive displacement syringe can hold from 1.0 μL to 1000 μL of biological sample, whereby the sample may be organic molecules, fluorogenic molecules, peptides, proteins, lipids, dilute solutions of polymers, liquid with coated microbeads, sample buffers, wash buffer biological cells and cell fractions. Each positive displacement pump delivers the sample to the site of aerosol generation. The positive displacement pump may be maintained in an environment that is refrigerated, at room temperature or heated. The positive displacement pump is controlled by a device that receives signals from a computer.

There are various ways to aerosolize the sample for application to the present system. One system relies on pressure nozzles, whereby the fluid sample to be aerosolized is pumped at high pressure through small orifice nozzles to generate an aerosol spray. In some nozzles, the fluid is carried by a pressurized inert carrier gas such as nitrogen, helium, air or oxygen. High velocity gas streams can be used to pull the fluid sample, by Bernoulli effect, into the nozzle and through the nozzle orifice. The carrier gas next delivers the aerosol to the biochip for deposition on the individual reaction dots. Nozzles may have internal components to facilitate aerosol formation. In one example, a small biological sample (0.1 to 1 ml) is pulled into a nozzle by pressurized gas flow (5 to 30 psig nitrogen) through a 250 micrometer orifice with a 210 micrometer inner needle to facilitate atomization.

Alternatively, spray aerosolization results from the use of ultrasonic nozzles which give low volumetric flow rate and uniform low velocity (under 10 cm/sec) mists. Ultrasonic standing waves within the nozzle cause atomization of the fluid at the tip of the nozzle. Low flow rates from 0.01 to 1000 μL/sec can be achieved by micropump delivery of sample into the nozzle body that contains a piezoelectric ultrasound transducer operating between 25 kHz to 240 kHz to create mists with average drop sizes from 5 to 15 micrometers in diameter. Energizing of the piezoelectric ultrasound transducer can utilize low wattage (from 0.1 to 25 watts) to avoid unwanted heating of the sample. For instance, a biological sample with the viscosity of 0.01 poise is pumped by a microsyringe pump at a flow rate of 0.1 to 1 μL/sec into an ultrasonic nozzle operating at 120 kHz (0.1 to 1 watt). Carrier gas streams external to the nozzle help to direct the mist to the bioreaction chip surface.

Another means of creating aerosolized sample relies on a contacting ultrasonic nebulizer where a fluid is placed in a well, the bottom of which contains an ultrasonic piezoelectric transducer. The transducer is operated at 1.0 to 3.0 MHz. The high frequency vibration at the top surface of the liquid in the sample chamber facilitates the formation of an atomized or nebulized cloud of fluid droplets. The action of nebulization causes the nebulized aerosol to rise from the chamber toward a bioreaction chip surface suspended atop the chamber. Additionally, a carrier gas can be introduced into the nebulizing chamber upwardly to displace the cloud. Alternatively, a carrier gas can be passed over the nebulizing chamber to pull the nebulized aerosol into the carrier stream by Bernoulli effect. The carrier gas is directed toward the samples to receive the aerosol. Atomized fluid particle diameter (d) is related by the surface tension (T), density (p), and the frequency (f) by the following approximate equation of: $d \sim (T/pf^3)^{1/3}$. For example, nebulization of water (T=0.0729 N/m, f=2.4 MHz) produces 1.7 micrometer mist droplets.

A further means of aerosol generation relies on a non-contacting ultrasonic nebulizer, in which a fluid to be delivered is placed in a tube that has a thin walled plastic bottom suitable for transmission of ultrasonic waves. The tube is placed in a conducting fluid that is in contact with the ultrasonic transducer and the fluid sample to be aerosolized, therefore, never comes in contact with the ultrasonic transducer per se. The transducer is generally operated between 1.0 to 3.0 MHz, and the high frequency vibration at the top surface of the liquid in the sample tube facilitates the formation of an atomized or nebulized cloud of fluid droplets in the sample tube. The action of nebulization can cause the nebulized aerosol to rise in the chamber and a carrier gas is delivered into the sample tube to displace the mist (optionally through a coarse collecting filter to remove large droplets) toward the bioreaction chip. Nebulized fluid samples prepared with this non-contacting ultrasonic nebulizer will generally have droplet sizes ranging from 1 to 25 micrometers.

Finally, ink-jet Piezo-printing, where delivery of a biological fluid into the printing head that exploits non-heating ink-jet technology may be used to propel the sample fluid toward a bioreaction spot. In the first approach of Piezo-printing, the printhead continually "prints" the biological fluid over the entire slide in a raster pattern of printing without discrimination of its position over the reaction spot or over glass. In this non-specific mode of operation, the ink-jet functions as a spray head, albeit one that creates a very narrow zone of spray and one that requires xy positioning with time over the bioreaction slide in order to actuate the entire slide. In this approach, the novel reaction zone isolation of the formulation fluid (glycerol) and the ability to print without forming a wetting film or a continuous layer of printed biological fluid allows reaction compartmentalization without spot-to-spot cross-bridging even though the entire surface is printed.

In the second approach of Piezo-printing, the printhead delivers biological fluid at discrete times. The delivery of a droplet of fluid to the reaction spot is triggered (1) by known information about its position relative to the known position of the reaction spots or (2) by sensing a property of the glycerol spot which triggers the delivery of fluid via ink-jet printing to the reaction spot. For example, a bifurcated fiber optic could excite a fluorescent dye in the reaction spot whose emission is transmitted via the fiber optic cable to an emission filter and a photomultiplier tube. The output of the photomultiplier tube is amplified, digitized and triggers the printing event. Alternatively, any optical property of the reaction spot can be sensed to trigger the activation of the bioreaction zones.

With any of the above-described sample application techniques or their equivalents, masking devices may be used to encourage sample application directly to the microdot. A masking device, such as a template or pattern, may be temporarily placed over dot array or microarray, or masking materials may be incorporated into the sample application equipment. Masking should be understood as optional to the present invention.

The assay is preferably contained within a computer-controlled gas flow rate metering system. A supply of inert carrier gas is supplied at high pressure with a regulator to control system pressure to under 50 psig. Typical pressure settings are between 5 to 15 psig. The gas flow uses the Bernoulli effect to put the aerosol stream toward the target slide to be activated. The carrier gas can be any of the following: air, oxygen, nitrogen, helium or argon. The gas flow rate can be between 0.1 and 5 L/min to help direct the aerosol from various nozzles. Alternatively, gas flow may be used to carry the liquid sample into the pressure nozzle by Bernoulli effect. It should be understood, however, that the use of these carrier gases is optional to the present method and apparatus.

For sample application and assay monitoring, the assay system preferably includes a computer controlled xy positioner with an independent x and y axis of movement. The xy positioner translates a removable stage that contains an accessible housing for assay chips ready for microdot application and assay activation. The removable stage allows transfer from the arrayer into the sprayer, and subsequently into the incubator while avoiding hands on contact between the operator and the individual slides. The xy positioner has a travel range from 0.1 m by 0.1 m up to 10 m by 10 m. Smaller distances of the xy positioner stage travel can be achieved by a linear stepper motor or servomotor. Longer distances can be achieved by motorized belt drive assemblies with motors that are controlled by individual drivers that receive driving signals from the main operating computer. A velocity of 0.1 to 20 in/sec can be achieved for rapid translation of slides under the aerosol.

Specifically, the assay method may involve dissolving a fluorogenic substrate in a volume of DMSO at 10 μM to 1 M concentration. A 0.1-1 volume of glycerol is then mixed with the substrate DMSO solution. This solution is delivered to a glass substrate by micromanipulation of a small diameter metal or plastic probe. The microdot can release its volatile DMSO component at room temperature. A mask is placed over the glass substrate to cover at least a portion of the areas among the microdots. A microspray of biological fluid is delivered through the mask to the microdots on the surface. The microdot array is incubated from 0 to 180 mins at 4-37° C. in 0 to 100% humidity. Conversion of substrate is detected in the microdot by excitation (350-400 nm) and emission above 420 nm using any available detection means.

It should be borne in mind that, in the practice of the present invention, the substrate need not start out as chromogenic or fluorogenic if it can be made so later in the process of assaying the sample. A second spray containing a reporter substrate is described to this end in Example 1 below.

Other than in the operating examples, or where otherwise indicated, all numbers expressing quantities of ingredients, reaction conditions and so forth used in the specification and claims are to be understood as being modified in all instances by the term "about." Accordingly, unless indicated to the contrary, the numberical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

In additional aspects, the present invention provides a method of transferring molecules of interest from an electrophoretic polymer gel to a MALDI target plate comprising the steps of:

(i) providing an electrophoretic gel containing one or more molecules of interest;

(ii) replacing water within the electrophoretic gel with a cosolvent mixture;

(iii) positioning a pin over the gel and penetrating the gel with the pin;

(iv) energizing the pin to deplete the gel in a region surrounding the one or more molecules of interest, causing the cosolvent mixture to surround the one or more molecules of interest;

(v) lifting the pin out of the gel, the pin carrying a drop of the cosolvent mixture containing the one or more molecules of interest; and (vi) contacting a MALDI target plate with the pin, the contacting causing the drop of cosolvent mixture containing the one or more molecules of interest to be deposited on the MALDI target plate. A schematic diagram illustrating this aspect is shown in FIG. 24.

Any method of gel electrophoresis separation can be used, so long as it provides adequate separation of the molecules of interest in the initial sample.

After separation of the molecules of interest, the gel is incubated in a water and polyol cosolvent mixture. Preferably, the polyol is glycerol, although other polyols having a viscosity, surface tension and vapor pressure similar to that of glycerol can be used. These properties provide the cosolvent mixture with the ability to adhere to the pin when the pin contacts the gel to remove a drop of fluid, and also permit the transfer of the drop to the target plate by adhesion of the drop to the target plate. These properties also ensure that a drop of the cosolvent mixture containing the one or more molecules of interest will maintain its position on the MALDI target plate, without substantial evaporation.

The cosolvent mixture is preferably 10% to 90% by volume polyol, usually 15% to 35% polyol. Water in the electrophoretic gel is replaced by the cosolvent mixture by incubating the gel in the mixture for a period of between 15-120 minutes.

The pin is a hollow or solid tipped pin as used in a standard microprinting or pin printing apparatus, as will be known to one skilled in the art. Preferably, the diameter of the pin at the tip (at the point of contact with the gel) is between 50 microns to 500 microns. Typically, the pin will be positioned over the gel in an area of high protein (or other molecule) concentration, as indicated by dye staining.

The pin is energized by ultrasound or other means. If ultrasound is used, the energy of the ultrasound vibration is between 0.1 and 5 watts per square centimeter, with a frequency between 10 kilohertz to 1 megahertz. The pin is energized for 10 seconds to 120 seconds.

Energizing the pin results in the depletion or collapse of the polymer gel in a region surrounding the pin. Cosolvent mixture and other fluids from the gel flow into the collapsed region and surround the one or more molecules of interest in the region surrounding the pin. Due to the viscosity, surface tension and vapor pressure of the cosolvent mixture, when the pin is lifted out of the gel the pin will carry a drop of the cosolvent mixture containing the one or more molecules of interest. This drop can then be deposited on a MALDI target plate, by contacting the plate with the. pin. The drop of cosolvent mixture containing the one or more molecules of interest will adhere to and be deposited on the MALDI target plate. The pin can then be washed in a submersion bath and the steps repeated one or more times to deposit a plurality of drops on the target plate. The word "drops" and "spots" will be used herein interchangeably to refer to the samples deposited on the MALDI target plate.

The drops of cosolvent mixture containing the molecules of interest deposited on the MALDI target plate by the methods of the present invention will be between 1 to 2000 nanoliters in size, more preferably between 1 to 100 nanoliters in size. The diameter of the drops will be between 50 and 500 microns, and the density of drops on the target plate is between 100 and 1000 drops per square centimeter.

After the drops are deposited on the target plate, a reagent chosen to react with the molecules of interest is deposited on the target plate, such that the reagent contacts the deposited drops containing the one or more molecules of interest and the reaction proceeds. The reagent can be deposited by standard methods known in the art, including but not limited to aerosol deposition, microprinting, pin printing, positive displacement pipetting and piezo printing.

The one or more molecules of interest include, but are not limited to, proteins, peptides, DNA, RNA, nucleotides, enzymes, amino acids, substrates, catalysts, salts, buffers, cofactors, reaction-altered chemical compounds, a member of a combinatorial library of chemical compounds, a component of a drug screening reaction and combinations thereof.

After the reactions have run to completion, the target plate with the deposited drops is prepared for MALDI mass spectrometry analysis by drying the deposited drops and coating the target plate with a MALDI matrix.

In a further aspect, the present invention provides a method of running chemical reactions on a MALDI target plate comprising: depositing drops of reactants on the target plate; depositing a reagent on the target plate such that the reagent contacts the deposited drops; and allowing the chemical reaction to proceed. The drops and the reagent are deposited on the target plate by any suitable means known in the art, including, but not limited to aerosol deposition, microprinting, pin printing, piezo printing, and positive displacement pipetting. Preferably, the volume of each deposited drop is between 1 to 2000 nanoliters, and also preferably, the density of drops on the target plate is between 100 and 1000 drops per square centimeter. Suitable reagents and reactants include, but are not limited to, proteins, peptides, DNA, RNA, nucleotides, enzymes, amino acids, substrates, catalysts, salts, buffers, cofactors, reaction-altered chemical compounds, a member of a combinatorial library of chemical compounds, a component of a drug screening reaction and combinations thereof.

In yet a further aspect, the present invention provides a method of preparing a sample for MALDI mass spectrometry analysis comprising the steps of:
(i) providing a target plate having liquid drops of sample;
(ii) drying the target plate to remove solvents from the sample drops;
(iii) depositing a MALDI matrix onto the dry target plate;
(iv) humidifying the target plate; and
(v) subjecting the target plate to MALDI mass spectrometry for analysis of the sample drops. These aspects of the invention are illustrated in the schematic diagram of FIG. 25.

The liquid sample drops comprise the reaction product of one or more reactants and one or more reagents. Suitable reactants and reagents include, but are not limited to, proteins, peptides, DNA, RNA, nucleotides, enzymes, amino acids, substrates, catalysts, salts, buffers, cofactors, reaction-altered chemical compounds, a member of a combinatorial library of chemical compounds, a component of a drug screening reaction and combinations thereof.

Preferably, the liquid sample drops have a volume of between 1-2000 nanoliters, and the density of liquid sample drops on the target plate is between 100 and 1000 drops per square centimeter.

The drying step is effected by any suitable method, such as vacuum drying or air drying.

Preferably, the matrix is deposited by aerosol deposition means, as is known in the art. Also preferably, the matrix is deposited in a layer of less than 50 microns in thickness, and less than 10 microliters of matrix is deposited per every 5 square centimeters of target plate. One or more layers can be deposited to achieve the desired thickness.

The matrix material comprises volatile solvents and a supersaturated concentration of matrix compounds. Matrix materials are well known in the art, and include but are not limited to the compositions listed in Tables 2 and 3, as described in *Matrix Materials for Matrix-Assisted Laser Desorption Ionization-Time of Flight (MALDI-TOF): Guidelines for Selection* (APPLIED BIOSYSTEMS—Voyager—DE—Biospectrometry Workstations).

TABLE 2

Commonly Used MALDI Matrices For Positive Ion Mode

α-cyano-4-hydroxycinnamic acid or HCCA a. 5-10 mg/ml of matrix in solution of 50:50 or 70:30 acetonitrile/aqueous 0.1% Trifluoroacetic acid
b. 5-10 mg/ml of matrix in solution of 60% ethanol/36% acetonitrile/4% water 2,5-Dihydroxybenzoic acid or DHB a. 5-10 mg/ml of matrix in solution of 10% aqueous ethanol TABLE 2-continued Commonly Used MALDI Matrices For Positive Ion Mode b. 5-10 mg/ml of matrix in solution of 50:50 or 70:30 acetonitrile/aqueous 0.1% Trifluoroacetic acid 3,5-Dimethoxy-4-hydroxycinnamic acid or sinapinic acid a. 5-10 mg/ml of matrix in solution of 50:50 acetonitrile/aqueous 0.1% Trifluoroacetic acid 2-(4-hydroxyphenylazo)benzoic acid or HABA a. 1.5 mg/ml of matrix in solution of 50:50 acetonitrile/water or 40:40:20 acetonitrile/methanol/water

TABLE 3

Commonly Used MALDI Matrices For Negative Ion Mode

α-cyano-4-hydroxycinnamic acid or HCCA a. 5-10 mg/ml of matrix in solution of 50:50 or 70:30 acetonitrile/aqueous 0.1% Trifluoroacetic acid
b. 5-10 mg/ml of matrix in solution of 60% ethanol/36% acetonitrile/4% water 2,5-Dihydroxybenzoic acid or DHB a. 5-10 mg/ml of matrix in solution of 10% aqueous ethanol
b. 5-10 mg/ml of matrix in solution of 50:50 or 70:30 acetonitrile/aqueous 0.1% Trifluoroacetic acid Hydroxypicolinic acid or HPA a. 25 mg/ml of matrix in solution of 50% acetonitrile with 2.5 mg/ml of diammonium tartrate or citrate 6-aza-2-thiothymine a. 10 mg/ml of matrix in solution of 50:50 acetonitrile/20 mM ammonium citrate The humidification step is carried out in a standard scientific humidification chamber at a relative humidity of 40% to 80%, at a temperature of 22° C. to 37° C. for a period of 10 minutes to 120 minutes. Care must be taken to ensure that humidification occurs without substantial deposition of water droplets on the MALDI matrix coating. Humidification causes the sample drops to become semi-solid and the constituents of the matrix are able to admix with the reaction products in the sample drops.

The matrix formed using the methods of the present invention provides detection of reaction products in the sample drops in the range of 1 to 50 femtomoles per sample drop. After deposition of the matrix, due to the ultrasmall drop size salt ions in the sample drops are able to diffuse away from the reaction products into the surrounding matrix, thus providing outstanding crystals for the subsequent MALDI MS analysis. Methods of the present invention can be used, for example, to detect activity of the drug on the molecule where the reactant is a biological molecule and the reagent is a drug.

In a further aspect, the present invention provides a method of depositing one or more layers of a MALDI matrix on a target plate comprising:
(i) providing a target plate having samples thereon;
(ii) aerosolizing the matrix; and
(iii) spraying the aerosolized matrix on the target plate while moving the target plate.

The matrix can aerosolized by standard methods known in the art, such as with an ultrasonic nozzle or a spray nozzle. Preferably, an ultrasonic nozzle is used, as it permits deposition of very small droplets and a very thin layer of matrix.

The gas flow rate of the ultrasonic nozzle or spray nozzle is between 0.1 to 5 microliters per minute, more preferably 0.5 to 2.0 microliters per minute. If an ultrasonic nozzle is used, preferably the energy of nozzle is set to between 0.1 to 2 watts, more preferably 0.5 to 1 watt. Preferably, the matrix is deposited at a thickness of less than 50 microns, and the target plate is moved at a rate of 0.1 to 5 inches per second, more preferably 0.5 to 2 inches per second, in a linear direction.

EXAMPLES

Example 1

A microarray of glycerol loci is created in which each glycerol spot (50 to 250 micrometers in diameter with a 50 to 500 micrometer space between spots) contains a single molecular species "A" such as a protein or protein fragment; a synthetic peptide; a small organic molecule; a nucleic acid sequence or a synthetic polymer. This species resides at a concentration between 10 picomolar and 10 millimolar within the spot. A 1"×3" glass slide is configured to yield over 10 $cm^2$ of arrayed glycerol loci at 100 to 1000 spots/$cm^2$.

An aerosol containing an enzyme (at 1 picomolar to 10 millimolar) is delivered to the array, whereby droplets of the enzyme fuse with the reaction spots while droplets that hit the slide quickly evaporate. For a period of time, the enzyme is allowed to come into binding equilibrium with the chemical species, typically 1 to 60 mins. A second spray contains a reporter system to detect the enzyme activity. Such a reporter system may consist of a fluorogenic substrate; a chromogenic substrate; a cofactor along with a detection system for cofactor conversion; or a cofactor and a substrate, whereby cofactor conversion produces a detectable signal. This reporter system can be delivered at concentrations from 10 nM to 100 mM with a fluorogenic substrate.

If the molecular species "A" binds the active site or an allosteric position of the enzyme "E", then the activation of the reporter system (e.g., conversion of a fluorogenic substrate) is prevented. Reaction zones that produce no reporter signal or reduced reporter signal are then identified as inhibitors of the enzyme. The inhibitor effect may be due to the molecular species "A" acting as a competitive inhibitor; a suicide inhibitor; a noncompetitive inhibitor; an allosteric modulator; a complexation agent against the substrate; an antagonist of cofactor binding; a complexation agent against the cofactor or an uncompetitive inhibitor.

Example 2

A microarray is set up to analyze binding events between antigens and antibodies. Initially, a polyclonal or monoclonal antibody is chemically linked to a colloidal object, such as colloidal gold (10 nM to 200 nM) or latex bead (10 nM to 200 nM). The latex beads with covalently linked antibodies are added to glycerol to create a suspension prepared for microarraying. The glycerol may also contain an unlinked polyclonal or monoclonal antibody against a particular antigen of detection. The concentration of the antibody covalently linked to the bead may range from 1 to 10,000 sites per square micron of the bead. The concentration of the free antibody in solution can range from 0 to 100 μM.

An array of spots is generated (spot size of 50 to 250 micrometer diameter with a 50 to 500 micrometer space between spots). Each spot has a unique composition whereby colloidal objects with linked antibody are maintained at a single concentration and the quenching free antibody is maintained at increasing concentration in a series of spots. A biological sample containing the antigen of detection is delivered via spray mechanism to the array. In each reaction spot, the quenching antibody binds the antigen (a faster reaction since the free antibodies have greater Brownian motion in comparison to the antibodies bound to the beads). If the concentration of the antigen exceeds the concentration of the quenching antibody, then free antigen remains and is available for binding to the beads. Beads will undergo antigen-mediated agglutination. The agglutinated colloidal gold or latex beads can be quantified by computer-assisted imaging of the aggregates, enhanced light scattering by aggregates or reduced light transmission by aggregates. Through use of known increasing concentrations of quenching antibodies in a series of spots, the concentration of antigen can be estimated to be equivalent to the minimum concentration of quenching antibody preventing agglutination.

Example 3

Detection of an antigen in a biological fluid is accomplished with a non-fluorescent species of unknown concentration. A series of glycerol droplets is arrayed with each containing a fluorescent species with a binding site. The reporter molecular would be under 30 kDa. Such a reporter molecule would be a GFP-ScFv chimeric protein where the single chain Fv fragment has high binding affinity for the antigen to be detected.

The antigen to be detected is sprayed onto the array surface and is sufficiently large (greater than 5 kDa) causing a significant change in the total molecular weight of the detector molecule/antigen complex. The detector molecule/antigen complex is analyzed by the polarization of the fluorescence emission of the complex which is greater than that of the reporter molecule alone when the system is excited with polarized light.

Example 4

Well characterized for over 30 years, serine proteases of the coagulation pathway in plasma were selected as a system in which to monitor the delivery of complex enzyme fluids to the microassay. Fluorogenic substrates in DMSO/glycerol were assayed to a glass slide.

After spray application, thrombin caused a 65-fold increase in fluorescence activity after conversion of the boc-VPR-MCA substrate. When deposited on the array, pure plasmin (1 μM) gave an intense signal for the boc-VLK-MCA substrate (25-fold above background) with detectable activity on the thrombin and kallikrein substrates. Plasmin has been reported to have activity on boc-VPR-MCA and Z-FR-MCA with no detectable activity on tPA and factor Xa substrates (Morita, 1977). Aerosol deposition of pure tPA (10 μM) to a sensing array caused significant cleavage of the tPA, thrombin and Xa substrates, resulting in fluorescence that was 18- to 20-fold above background.

The microarray detected the modest activation of the coagulation pathway in recalcified diluted plasma due to low level factor Xa and thrombin activity (Butenas, 1997; Rand, 1996). Since corn trypsin inhibitor was not present to inhibit factor XIIa (Rand, 1996), moderate activation of the contact system and kallikrein generation was detected by conversion of the kallikrein substrate. Recalcified citrated plasma does not generate plasmin in excess of the ∀2-antiplasmin and ∀2-macroglobulin consistent with the lack of conversion of the plasmin substrate. The microarray revealed that the conversion of kallikrein substrate occurred from the contact activation of prekallikrein to kallikrein, not from non-specific Z-FR-MCA substrate cleavage by plasmin.

Addition of plasmin (0.43 µM final concentration) to the diluted recalcified citrated plasma overcame inhibitory concentrations of ∀2-antiplasmin and ∀2-macroglobulin. This plasmin activity was detected by a strong signal in the plasmin substrate spot. Plasmin can inactivate factor Xa (Pryzdial, 1999) and this reduction in factor Xa activity was observed in the microassay. Plasmin is also a potent activator of factor XU to factor XUa which can in turn convert prekallikrein to kallilkrein. A high level of kallilkrein substrate conversion was noted in the plasmin treated-plasma beyond that expected from plasmin-mediated conversion of the kallikrein substrate. Addition of a higher level of plasmin (2.14-1 µM final concentration) led to significant cleavage of each substrate on the array. The microarray revealed that plasmin-mediated activation of factor XIIa resulted in kallikrein production with sufficiently increased intrinsic pathway production of factor Xa to overcome plasmin-mediated factor Xa proteolysis to factor Xaa.

Example 5

Programmed cell death (apoptosis) can be triggered by various cellular events such as calcium influx; oxidative stress; cytoskeletal interference; inhibitors of protein synthesis; membrane disruption or DNA disruption. Numerous chemicals induce apoptosis in specific cell types and include receptor ligands (TRAIL, FasL); ceremide-based lipids; taxol; vinblastine; cytochalasin D; topoisomerase inhibitors (etoposide); DNA cross linking agents; protein kinase inhibitors and mitochondria permeability agents (betulinic acid, rotenone).

Apoptosis occurs after activation/aggregation of surface receptors. The best studied death receptors are TNFR1 (p55 or CD120a) and CD95 (FasR or Apo1). Other death receptors include DR3 (Apo3), DR4 and DR5 (TRAIL-R2, Apo2). In cancer therapeutics, soluble TRAIL (Apo2L) can bind its receptors DR4 and DR5 to activate apoptosis in transformed cell lines but not in normal cells. Downstream signaling of death receptors is well understood, but complex. As an example, homotrimeric CD95L binds CD95 which undergoes clustering and subsequent binding of a Fas-associated death domain (FADD) protein which in turn activates Caspase 8 (FLICE). After oligomerization, Caspase 8 undergoes autoactivation which in turn activates Caspase 9. Pathways distal to TNF binding TRNR1, Apo3L binding to DR3, and Apo2L binding DR4 or DRS result in multimerization of receptors, adaptors and activation of caspases. Several caspases can proteolytically inactivate poly(ADP-ribose) polymerase (PARP) and degrade nuclear lamin which are key signatures of apoptosis.

The role of the mitochondria in apoptosis is thought to result from the ancient two-billion year old symbiosis that produced eucaryotic cells. Loss of mitochondria integrity disrupts energy (ATP) production, triggers caspase activation and disturbs the redox potential of the cell. In caspase activation, cytochrome c (blocked by apoptosis inhibitor bcl-2) released from the mitochondria can complex with Apaf-1 and Procaspase 9 resulting in activation of Caspase 9.

Caspases (cysteinyl aspartate-specific proteases) cleave protein substrates on the carboxyl terminus side of aspartate (P1 position). Positions P2, P3 and P4 also contribute to substrate specificity with P4 residues having the largest role in dictating substrate preferences among the caspases. A total of 13 distinct caspases have been identified so far. Various caspases can cleave a given fluorogenic substrate and the use of the term "a Caspase 3 substrate" does not imply that other caspases do not cleave this substrate or that Caspase 3 does not cleave other substrates. The substrate specificity of caspases has been studied through the synthesis of chromogenic and fluorogenic peptide libraries (Talanian, 1997; Thomberry, 1997). Thornberry used a 60-compound fluorogenic positional scanning library Ac—X—X—X-Asp-AMC to evaluate the specificity in brackets of Caspase 1 [WEHD]; Caspase 2 [DEHD]; Caspase 3 [DEVD]; Caspase 4 [(W/L)EHD]; Caspase 5 [(W/L)EHD]; Caspase 6 [VEHD]; Caspase 7 [DEVD], Caspase 8 [LETD]; Caspase 9 [LEHD] and Granzyme B [IEPD]. Similarly, various peptide aldehydes have been tested for specificity of inhibition (Garcia-Calvo, 1998) with second order rate constants $>10^5$ $M^-s^{-1}$.

TABLE 1

| Substrate/Inhibitor | IETD-CHO I6 | VDVAD-CHO I5 | DEVD-CHO I4 | YVAD-CHO I3 | LEHD-CHO I2 | VEID-CHO I1 | Blank |
|---|---|---|---|---|---|---|---|
| VEID | S1 + I6 | S1 + I5 | S1 + I4 | S1 + I3 | S1 + I2 | S1 + I1 | S1 |
| LEHD | S2 + I6 | S2 + I5 | S2 + I4 | S2 + I3 | S2 + I2 | S2 + I1 | S2 |
| YVAD | S3 + I6 | S3 + I5 | S3 + I4 | S3 + I3 | S3 + I2 | S3 + I1 | S3 |
| DEVD | S4 + I6 | S4 + I5 | S4 + I4 | S4 + I3 | S4 + I2 | S4 + I1 | S4 |
| VDVAD | S5 + I6 | S5 + I5 | S5 + I4 | S5 + I3 | S5 + I2 | S5 + I1 | S5 |
| IETD | S6 + I6 | S6 + I5 | S6 + I4 | S6 + I3 | S6 + I2 | S6 + I1 | S6 |

Example 6

A biological fluid is delivered to the chip surface as an aerosol where the fluid is a liquid sample obtained from blood; urine; saliva; biopsy; microbe or microbial preparation; virus or viral preparation; cell lysate or cell suspension or a food or agricultural product. Alternatively, the aerosol may be composed of a carrier gas such as air or nitrogen mixed with a sample gas in which are dispersed protein, viral or bacterial particles. The sample is tested for enzymatic activity where fluorogenic substrates have been arrayed in glycerol MCA substrates and enzymes.

Example 7

A suspension of cells, DNA, total RNA or MRNA is delivered to reaction zones arrayed on a microassay chip. Individual reaction zones contain PCR primers; reverse transcriptase primers; dye-labeled oligo sequences; nucleic acid bases or fluorescent bases and enzymes such as reverse transcriptase; DNA polymerase; RNAse; DNAse; heat stable DNA polymerase or cleavase enzyme. The chip is subjected to heat cycles for PCR or nucleic acid synthesis or fluorescence tag incorporation or fluorescence activation of quenched entities via sequence dependent reactions. Subsequent detection can involve energy transfer between two independent fluorescent probes brought into proximity by a sequence dependent reaction dequenching of quenched molecules due to a sequence dependent reaction. Applications can include phenotypic analysis of MRNA species, genotypic analysis of DNA species and detection of single nucleotide polymorphisms (SNPs).

Example 8

Microarrays have numerous applications in protease engineering and proteomics. A constant P1 positional scanning library of fluorogenic peptides with 19 different amino acids at the P2, P3 or P4 position (57 sublibraries) (Backes, 2000) can be accommodated by <1 cm$^2$ of microarray with minimal usage of reagents. An entire scanning fluorogenic library (Harris, 2000) with 19 to 20 different amino acids in the P1-P4 positions (<1200 spots) could be accommodated on a 1"×3" slide well within the capability of glycerol spotting and aerosol deposition technology. In this example, a single protease is applied to individual fluorogenic substrates arrayed on the chip from a positional scanning library. Conversion of substrates and substrate specificity can be determined on a single microassay chip. Also, a combinatorial library of fluorogenic peptides where the identity of each amino acid in each position is well-established can be employed on a microassay chip.

Example 9

Removal of Sample from Gel and Transfer to MALDI Target Plate

For direct detection, 1 ug of purified human fibrinogen per lane is heated to 95° C. for 5 min in SDS running buffer (Tris-EDTA, pH 8.0, 2% vol/vol SDS, 8 M urea). The protein sample is run on a one dimensional 4-15% gradient polyacrylamide gel and then stained with commassie blue dye for 60 min, the position of the band noted, and the gel destained with NH4/HC03/50% acetonitrile, followed by incubation in 30% by vol. glycerol for 120 min at room temperature with gentle orbital mixing. The gel is briefly rinsed with distilled water and a pin is positioned above the location of the protein band, and submerged halfway into the gel and energized by coupling to an ultrasonic transducer (30 kHz, Sonicare) for 20 sec. The pin is slowly removed from the gel and placed in contact with the metal MALDI target surface by contact printing (GeneMachines Ascent). A single pin protocol using stealth SMP15XB pins from Telechem (Sunnyvale, Calif.) is used to print a 500 um spot, onto the SS plate using the OmniGrid Accent microarrayer from Genemachines (now part of Genomic Solutions, Ann Arbor, Mich.). For proteolytic digestion, the fibrinogen is then activated with 10 uM of human thrombin (50 mM Sodium Citrate, 0.2 M NaCl, 0.1% PEG-8000 and pH 6.5). Human thrombin is delivered to the array via a 120 kHz ultrasonic nozzle (Sonotek, Milton, N.Y.). The sample is aerosolized at a liquid flow rate of 400 nl/s into the nozzle using a UMPII flow pump (World Precision Instruments, Saratoga, Fla.) and sheathed with a carrier air flow of 2.3 L/min. After aerosol deposition for 2 or 4 s, the SS plate with the reactions is incubated at 37° C. for 4 hrs. The reaction is then stopped by overnight extraction of glycerol leaving behind fine crystals of the cleavage product of fibrinogen in presence of thrombin: fibrinopeptide A (Avg. MW: 1536.57 Da) and fibrinopeptide B (Avg. MW: 1569.60 Da). The cleavage products are detected using the Voyager DE—PRO matrix-assisted-laser-desoprtion-ionization time-of-flight (MALDI TOF) mass spectrometer (MS) from Applied Biosystems (Foster City, Calif.). For detection purposes the plate is coated with a thin film of 3,5-Dimethoxy-4-hydoxycinnamic acid (sinapinic acid) in 50% ethanol. This is a typical positive ion mode matrix used for MALDI TOF MS. The MS is used in the positive linear mode with the laser source maintained at a constant power for al detection. The peaks for fibrinopeptide A and B are obtained at their respective m/z mass ranges (data not shown).

Example 10

High Throughput Screening

The ability to run nanoliter reactions using libraries printed on flat surfaces allows for the use of MALDI mass spectrometry to probe HTS reactions. The feasibility of running label-free reactions by printing fibrinogen solutions on a metal MALDI target, followed by aerosol deposition of thrombin to release fibrinopeptides A and B, has been demonstrated. The glycerol in the reaction was then removed, and MALDI matrix was deposited to result in a thin film suitable (FIG. 26A) for MS detection of FPA/FPB. Benzamidine in the nanoliter reaction completely inhibited the reaction (FIG. 26B). These sensitivity of MALDI to detect calibrants and converted substrates in the range of 3 to 300 nM is ideal for the typical reaction conditions needed in HTS assays.

A 8×12 array of reactions were printed using an OmniGrid microarrayer containing varying concentrations of fibrinogen and a fibrinopeptide MS satandard. Certain reactions contained 1 mM benzamidine. The array was activated with thrombin and incubated under humidity (top row, A), the glycerol was removed (middle row, A), and then coated with MALDI matrix (bottom row, A). Individual reactions were then subjected to MALDI for analysis of fibrinopeptides A and B. A large signal was seen at 1, 10, and 100 ug/ml of fibrinogen (3, 30 and 300 nM) treated with thrombin, but not in screening reactions containing benzamidine (B). Conditions of the MALDI MS were: Voyager—DE PRO (sinapinic acid matrix), Glu1-Fibrinopeptide B (1 ug/ml) control, Reflector Mode, Positive Polarity, 1000-2000 Da Acquisition Range, 20000 V Accelerating voltage, 2033 laser. intensity (20.0 Hz; 100/spectrum), Extraction delay time: 150 nsec, Grid voltage: 75%, Guide wire voltage: 0.002%.

Example 11

Detection of Protein/Enzyme Interaction

Plasminogen depleted human fibrinogen (MW: 330 kDa) was purchased from Enzyme Research Labs (South Bend, Ind.). It was aliquoted in the manufacturer recommended buffer of 10 mM Phosphate, 20 mM Citrate, 0.15 M NaCl (pH 7.4) at a concentration of 36 mg/ml. Six fold dilutions—18 mg/ml, 9 mg/ml, 4.5 mg/ml, 3 mg/ml, 1.5 mg/ml and 0.75 mg/ml of 1:1 plasminogen depleted fibrinogen and glycerol were performed and aliquoted separately. Twelve replicates of each solution were then printed in on to a single blank stainless steel (SS) mass spectrometry plate from Applied Biosystems (Foster City, Calif.). A single pin protocol using stealth SMP15XB pins from Telechem (Sunnyvale, Calif.) was used to print 500 um spots, onto the SS plate using the OmniGrid Accent microarrayer from Genemachines (now part of Genomic Solutions, Ann Arbor, Mich.). The spot to spot spacing was 1000 um.

The fibrinogen was then activated with 10 uM of human thrombin (50 mM Sodium Citrate, 0.2 M NaCl, 0.1% PEG-8000 and pH 6.5). Human thrombin was delivered to the array via a 120 kHz ultrasonic nozzle (Sonotek, Milton, N.Y.). The sample was aerosolized at a liquid flow rate of 400 nl/s into the nozzle using a UMPII flow pump (World Precision Instruments, Saratoga, Fla. and sheathed with a carrier air flow of 2.3 L/min. After aerosol deposition for 2 or 4 s, the SS plate with the reactions was incubated at 37° C. for 4 hrs. The reaction was then stopped by overnight extraction of glycerol leaving behind fine crystals of the cleavage product of fibrinogen in presence of thrombin: fibrinopeptide A (Avg. MW: 1536.57 Da). and fibrinopeptide B (Avg. MW: 1569.60 Da).

The cleavage products were detected using the Voyager DE—PRO matrix-assisted-laser-desoprtion-ionization time-of-flight (MALDI TOF) mass spectrometer (MS) from Applied Biosystems (Foster City, Calif.). For detection purposes the plate was coated with a thin film of 3,5-Dimethoxy-4-hydoxycinnamic acid (sinapinic acid) in 50% ethanol. This is a typical positive ion mode matrix used for MALDI TOF MS. The MS was used in the positive linear mode with the laser source maintained at a constant power for al detection. The peaks were for fibrinopeptide A and B were obtained at their respective m/z mass ranges. Mass spectrum data is presented in FIGS. 27 A-O for the 18 mg/ml, 3 mg/ml and 0.75 mg/ml samples.

Although the invention has been described above with reference to particular materials and methods, the invention is only to be limited insofar as is set forth in the accompanying claims.

The invention claimed is:

1. A method of transferring molecules of interest from an electrophoretic polymer gel to a MALDI target plate comprising the steps of: (i) providing an electrophoretic gel containing one or more molecules of interest; (ii) incubating the electrophoretic gel with a cosolvent mixture; (iii) positioning a pin over the gel and penetrating the gel with the pin; (iv) energizing the pin to deplete the gel in a region surrounding the one or more molecules of interest, causing the cosolvent mixture to surround the one or more molecules of interest; (v) lifting the pin out of the gel, the pin carrying a drop of the cosolvent mixture containing the one or more molecules of interest; and (vi) contacting a MALDI target plate with the pin, the contacting causing the drop of cosolvent mixture containing the one or more molecules of interest to be deposited on the MALDI target plate.

2. The method of claim 1, wherein the viscosity, surface tension and vapor pressure of the cosolvent mixture cause the drop of cosolvent mixture containing the one or more molecules of interest in the gel to adhere to the pin.

3. The method of claim 1, wherein the viscosity, surface tension and vapor pressure of the cosolvent mixture cause the drop of cosolvent mixture containing the one or more molecules of interest to be transferred to and adhere to the MALDI target plate from the pin.

4. The method claim 1, wherein the viscosity, surface tension and vapor pressure of the cosolvent mixture cause the drop of cosolvent mixture containing the one or more molecules of interest to maintain its position on the MALDI target plate, without substantial evaporation.

5. The method of claim 1, wherein the cosolvent mixture is a water and glycerol mixture of 10% to 90% by volume glycerol.

6. The method of claim 1, wherein the cosolvent mixture is a water and polyol mixture.

7. The method of claim 1, wherein the energizing of the pin is effected by ultrasound vibration.

8. The method of claim 7, wherein the energy of the ultrasound vibration is between 0.1 and 5 watts per square centimeter.

9. The method of claim 7, wherein the frequency of the ultrasound vibration is between 10 kilohertz to 1 megahertz.

10. The method of claim 1, wherein the pin is energized for 10 seconds to 120 seconds.

11. The method of claim 1, wherein the diameter of the pin at the tip is between 50 microns to 500 microns.

12. The method of claim 1, wherein the drop of cosolvent mixture containing the one or more molecules of interest is between 1 to 2000 nanoliters in size.

13. The method of claim 1, wherein the drop of cosolvent mixture containing the one or more molecules of interest is between 1 to 100 nanoliters in size.

14. The method of claim 1, wherein the diameter of the drop deposited on the MALDI target plate is between 50 and 500 microns.

15. The method of claim 1, further comprising (vii) washing the pin in a submersion bath and repeating, the steps one or more times to deposit a plurality of drops on the target plate.

16. The method of claim 15, wherein the density of drops on the target plate is between 100 and 1000 drops per square centimeter.

17. A method of performing a reaction on a MALDI target plate comprising:

providing an electrophoretic gel containing one or more molecules of interest;

incubating the electrophoretic gel with a cosolvent mixture;

positioning a pin over the gel and penetrating the gel with the pin;

energizing the pin to deplete the gel in a region surrounding the one or more molecules of interest, causing the cosolvent mixture to surround the one or more molecules of interest;

lifting the pin out of the gel, the pin carrying drop of the cosolvent mixture containing the one or more molecules of interest;

contacting a MALDI target plate with the pin, the contacting causing the drop of cosolvent mixture containing the one or more molecules of interest to be deposited on the MALDI target plate;

depositing a reagent on the target plate, such that the reagent contacts the deposited drops of cosolvent mixture containing the one or molecules of interest; and allowing the reagent to react with the one or molecules of interest in the deposited drops.

18. The method of claim 17, wherein the depositing of the reagent is effected by a means selected from the group consisting of aerosol deposition, microprinting, pin printing, positive displacement pipetting and piezo printing.

19. The method of claim 1, wherein the one or more molecules of interest are selected from the group consisting of proteins, peptides, DNA,RNA, nucleotides, enzymes, amino acids, substrates, catalysts, salts, buffers, cofactors, reaction-altered chemical compounds, a member of a combinatorial library of chemical compounds, a component of a drug screening reaction and combinations thereof.

20. The method of claim 1, wherein the incubating is for a period of between 15-120 minutes.

21. A method of preparing a sample for MALDI mass spectrometry analysis comprising:
   (i) providing an electrophoretic gel containing one or more molecules of interest;
   (ii) incubating the electrophoretic gel with a cosolvent mixture;
   (iii) positioning a pin over the gel and penetrating the gel with the in;
   (iv) energizing the pin to deplete the gel in a region surrounding the one or more molecules of interest, causing the cosolvent mixture to surround the one or more molecules of interest;
   (v) lifting the pin out of the gel, the pin carrying a drop of the cosolvent mixture containing the one or more molecules of interest;
   (vi) contacting a MALDI target plate with the pin, the contacting causing the drop of cosolvent mixture containing the one or more molecules of interest to be deposited the MALDI target plate;
   (vii) washing the pin in a submersion bath;
   (viii) repeating (i) through (vi) one or more times to deposit a plurality of on the target plate; and
   (ix) preparing the target plate with the deposited drops for MALDI mass spectrometry analysis by drying the deposited drops and coating the target plate with a MALDI matrix.

22. The emthod of claim 21, wherein the drying of step (ix) comprises vacuum drying and the coating of step (ix) comprises spray coating.

* * * * *